(12) United States Patent
Tamaru et al.

(10) Patent No.: US 9,359,627 B2
(45) Date of Patent: Jun. 7, 2016

(54) ANTIBODY PRODUCTION METHOD

(75) Inventors: Yutaka Tamaru, Mie (JP); Hiroko Tsutsumi, Kyoto (JP)

(73) Assignee: NATIONAL UNIVERSITY CORPORATION MIE UNIVERSITY, Mie (JP)

( * ) Notice: Subject to any disclaimer, the term of this patent is extended or adjusted under 35 U.S.C. 154(b) by 0 days.

(21) Appl. No.: 14/005,411

(22) PCT Filed: Mar. 15, 2012

(86) PCT No.: PCT/JP2012/056691
§ 371 (c)(1),
(2), (4) Date: Nov. 25, 2013

(87) PCT Pub. No.: WO2012/124764
PCT Pub. Date: Sep. 20, 2012

(65) Prior Publication Data
US 2014/0100358 A1 Apr. 10, 2014

(30) Foreign Application Priority Data
Mar. 17, 2011 (JP) .................................. 2011-059739

(51) Int. Cl.
*A61K 39/39* (2006.01)
*C12P 21/00* (2006.01)
*C07K 16/00* (2006.01)
*C07K 16/12* (2006.01)
*C07K 16/40* (2006.01)
*C07K 16/18* (2006.01)
*C07K 16/28* (2006.01)

(52) U.S. Cl.
CPC ............... *C12P 21/005* (2013.01); *C07K 16/00* (2013.01); *C07K 16/1289* (2013.01); *C07K 16/18* (2013.01); *C07K 16/2869* (2013.01); *C07K 16/40* (2013.01); C07K 2317/20 (2013.01)

(58) Field of Classification Search
None
See application file for complete search history.

(56) References Cited

U.S. PATENT DOCUMENTS

| 6,669,947 | B2 | 12/2003 | Barnett et al. |
| 6,833,134 | B2 | 12/2004 | Bolton et al. |
| 7,273,930 | B2 | 9/2007 | Bolton et al. |
| 7,749,516 | B2 | 7/2010 | Bolton et al. |
| 7,807,169 | B2 | 10/2010 | Barnett et al. |
| 2002/0090375 | A1 | 7/2002 | Barnett et al. |
| 2003/0165524 | A1 | 9/2003 | Bolton et al. |
| 2004/0022798 | A1 | 2/2004 | Barnett et al. |
| 2005/0026248 | A1* | 2/2005 | Hsueh et al. ................. 435/69.1 |
| 2005/0089529 | A1 | 4/2005 | Bolton et al. |
| 2008/0213294 | A1 | 9/2008 | Bolton et al. |
| 2010/0028379 | A1 | 2/2010 | Tucker et al. |
| 2012/0135422 | A1 | 5/2012 | Tamaru |
| 2015/0182619 | A1 | 7/2015 | Tucker et al. |

FOREIGN PATENT DOCUMENTS

| JP | 2001-86992 A | 4/2001 |
| JP | 2007-255892 A | 10/2007 |
| JP | 2009-73783 A | 4/2009 |
| JP | 2009-183151 A | 8/2009 |
| WO | 98/18323 | 5/1998 |
| WO | 2010/113988 A1 | 10/2010 |

OTHER PUBLICATIONS

International Search Report for International Appl. No. PCT/JP2012/056691, mailed Apr. 10, 2012.
International Preliminary Report on Patentability for International Appl. No. PCT/JP2012/056691, mailed Sep. 26, 2013.
Hisayoshi Ishikawa et al., "Hito GPCR ni Taisuru Gyorui Kotai Sakuseiho no Kaihatsu", 32nd Annual Meeting of the Molecular Biology Society of Japan Koen Yoshishu, 2009, p. 1P-0849, along with an English language translation.

* cited by examiner

*Primary Examiner* — Michael Pak
(74) *Attorney, Agent, or Firm* — Greenblum & Bernstein, P.L.C.

(57) ABSTRACT

Provided is an antibody production method whereby it is possible to repeatedly acquire antibodies produced by fish without killing the fish. Specifically provided is an antibody production method whereby it is possible to repeatedly acquire the antibodies produced by a fish, without killing the fish, by administering antigens to fish that have blisters.

7 Claims, 9 Drawing Sheets

Fig.1
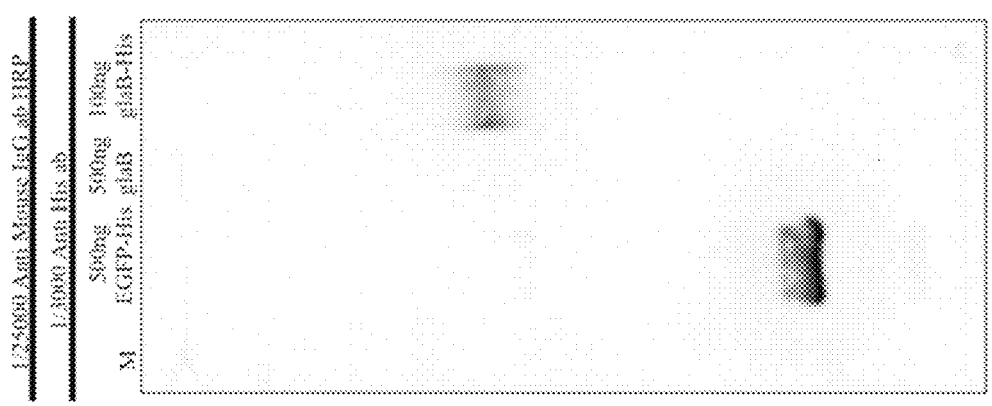
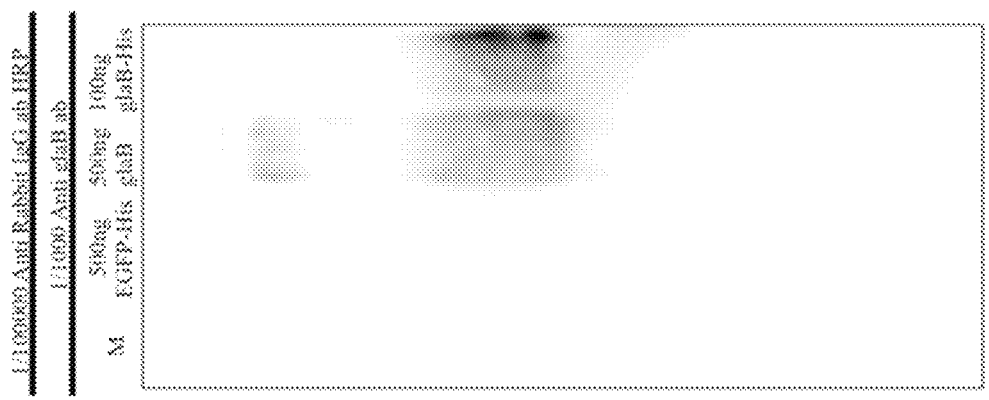

```
       250       260       270       280       290       300
       aagaggtaatacaccATGAATCACAAAGTGCATCATGATCATCATCAGATGCAAGTTTCA
                     M  N  H  K  V  H  H  H  H  H  H  N  Q  V  S
                                      [His Tag]

310       320       330       340       350       360
       GTTGAAACCACTCAAGGGCTTGGCCGCCGTGTAACGATTACTATCGCTGCTGACAGCATC
        V  E  T  T  Q  G  L  G  R  R  V  T  I  T  I  A  A  D  S  I
       [Trigger Factor]

370       380       390       400       410       420
       GAGACCGCTGTTAAAAGCGAGCTGGTCAACGTTGCGAAAAAAGTACGTATTGACGGCTTC
        E  T  A  V  K  S  E  L  V  N  V  A  K  K  V  R  I  D  G  F 430       440       450       460       470       480
       CGGCAAGGGCAAAGTGCCAATGAATATCGTTGCTCAGCGTTATGGCGCGTCTGTACGCCAG
        R  K  G  K  V  P  M  N  I  V  A  Q  R  Y  G  A  S  V  R  Q 490       500       510       520       530       540
       GACGTTCTGGGTGACCTGATGAGCCGTAACTTCATTGACGCCATCATTAAAGAAAAAATC
        D  V  L  G  D  L  M  S  R  N  F  I  D  A  I  I  K  E  K  I 550       560       570       580       590       600
       AATCCGGCTGGCGCACCGACTTATGTTCCGGGCGAATACAAGCTGGGTGAAGACTTCACT
        N  P  A  G  A  P  T  Y  V  P  G  E  Y  K  L  G  E  D  F  T 610       620       630       640       650       660
       TACTCTGTAGAGTTTGAAGTTTATCCGGAAGTTGAACTGCAAGGTCTGGAAGCGATCGAA
        Y  S  V  E  F  E  V  Y  P  E  V  E  L  Q  G  L  E  A  I  E
                                                              / Pvul 670       680       690       700       710       720
       GTTGAAAAACCGATCGTTGAAGTGACCGACGCTGACGTTGACGGCATGCTGGATACTCTG
        V  E  K  P  I  V  E  V  T  D  A  D  V  D  G  M  L  D  T  L
       / Pvul 730       740       750       760       770       780
       CGTAAACAGCAGGCGACCTGGAAAGAAAAAGACGGGCGCTGTTGAAGCAGAAGACCGCGTG
        R  K  Q  Q  A  T  N  K  E  K  D  G  A  V  E  A  E  D  R  V 790       800       810       820       830       840
       ACCATCGACTTCACCGGTTCTGTAGACGGCGAAGAGTTCGAAGGCGGTAAAGCGTCTGAT
        T  I  D  F  T  G  S  V  D  G  E  E  F  E  G  G  K  A  S  D
                                  / Accl 850       860       870       880       890       900
       TTCGTACTGGCGATGGGCCAGGGTCGTATGATCCCGGGCTTTGAAGACGGTATCAAAGGC
        F  V  L  A  M  G  Q  G  R  M  I  P  G  F  E  D  G  I  K  G
                                          / Smal             BstXI 910       920       930       940       950       960
       CACAAAGCTGGCGAAGAGTTCACCATCGACGTGACCTTCCCGGAAGAATACCACGCAGAA
        H  K  A  G  E  E  F  T  I  D  V  T  F  P  E  E  Y  H  A  E
       /

970       980       990      1000      1010      1020
       AACCTGAAAGGTAAAGCAGCGAAATTCGCTATCAACCTGAAGAAAGTTGAAGAGCGTGAA
        N  L  K  G  K  A  A  K  F  A  I  N  L  K  K  V  E  E  R  E 1030      1040      1050      1060      1070      1080
       CTGCCGGAACTGACCGCAGAGTTCATCAAACGTTTCGGCGTTGAAGATGGTTCCGTAGAA
        L  P  E  L  T  A  E  F  I  K  R  F  G  V  E  D  G  S  V  E 1090      1100      1110      1120      1130      1140
       GGTCTGCGCGCTGAAGTGCGTAAAAACATGGAGCGCGAGCTGAAGAGCGCCATCCGTAAC
        G  L  R  A  E  V  R  K  N  M  E  R  E  L  K  S  A  I  R  N 1150      1160      1170      1180      1190      1200
       CGCGTTAAGTCTCAGGCGATCGAAGGTCTGGTAAAAGCTAACGACATCGACGTACCGGCT
        R  V  K  S  Q  A  I  E  G  L  V  K  A  N  D  I  D  V  P  A
               / Pvul 1210      1220      1230      1240      1250      1260
       GCGCTGATCGACAGCGAAATCGACGTTCTGCGTCGCCAGGCTGCACAGCGTTTCGGTGGC
        A  L  I  D  S  E  I  D  V  L  R  R  Q  A  A  Q  R  F  G  G
```

```
       1270      1280      1290      1300      1310      1320
       AACGAAAAACAAGCTCTGGAACTGCCGCGCGGAACTGTTCGAAGAACAGGCTAAAACGCCGC
        N  E  K  Q  A  L  E  L  P  R  E  L  F  E  E  Q  A  K  R  R 1330      1340      1350      1360      1370      1380
       GTAGTTGTTGGCCTGCTGCTGGGCGAAGTTATCCGCACCAACGAGCTGAAAGCTGACGAA
        V  V  V  G  L  L  L  G  E  V  I  R  T  N  E  L  K  A  D  E 1390      1400      1410      1420      1430      1440
       GAGCGCGTGAAAGGCCTGATCGAAGAGATGGCTTCTGCGTACGAAGATCCGAAAGAAGTT
        E  R  V  K  G  L  I  E  E  M  A  S  A  Y  E  D  P  K  E  V 1450      1460      1470      1480      1490      1500
       ATCGAGTTCTACAGCAAAAACAAAGAACTGATGGACAACATGCGCAATGTTGCTCTGGAA
        I  E  F  Y  S  K  N  K  E  L  M  D  N  M  R  N  V  A  L  E 1510      1520      1530      1540      1550      1560
       GAACAGGCTGTTGAAGCTGTACTGGCGAAAGCGAAAGTGACTGAAAAAGAAACCACTTTC
        E  Q  A  V  E  A  V  L  A  K  A  K  V  T  E  K  E  T  T  F 1570      1580      1590      1600      1610      1620
       AAGGAGCTGATGAACCAGCAGGCGTCCGCGGGTCTGGAAGTTCTGTTCCAGGGGCCCTCC
        N  E  L  M  N  Q  Q  A  S  A  G  L  E  V  L  F  Q  G  P  S
                                                      / SacII            SacII 1630      1640      1650      1660      1670      1680
       GCGGGTCTGGTGCCACGCGGTAGTGGTGGTATCGAAGGTAGGCATATATGGAGCTCGGTA
        A  G  L  V  P  R  G  S  G  G  I  E  G  R  H  I  W  S  S  V
                                                          / SacI Kpnl 1690      1700      1710      1720      1730      1740
       CCCTCGAGGGATCCATCACACTCCTTCTACAATTTGAGTAAAGTGACTCACATAGAAATT
        P  S  R  D  P ░░░░░░░░░░░░░░░░░░░░░░░░░░░░░░░░░░░░░░░░░
       // /       [hLGR3]
       Xhol  BamHI 1750      1760      1770      1780      1790      1800
       CGGAATACCAGGAACTTAACTTACATAGACCCTGATGCCCTCAAAGAGCTCCCCCTCCTA
                                                      / SacI 1810      1820      1830      1840      1850      1860
       AAGTTCCTTGGCATTTTCAACACTGGACTTAAAATGTTCCCTGACCTGACCAAAGTTTAT 1870      1880      1890      1900      1910      1920
       TCCACTGATATATTCTTTATACTTGAAATTACAGACAACCCTTACATGACGTCAATCCCT
                                                              / AatII 1930      1940      1950      1960      1970      1980
       GTGAATGCTTTTCAGGGACTATGCAATGAAACCTTGACACTGAAGCTGTACAACAACGGC 1990      2000      2010      2020      2030      2040
       TTTACTTCAGTCCAAGGATATGCTTTCAATGGGACAAAGCTGGATGCTGTTTACCTAAAC 2050      2060      2070      2080      2090      2100
       AAGAATAAATACCTGACAGTTATTGACAAAGATGCATTTGGAGGAGTATACAGTGGACCA
                                                        / Accl        HindIII 2110      2120      2130      2140      2150      2160
       AGGTTGCTGGACCTGTCTCAAACCAGTGTCACTGCCCTTCCATCCAAAGGGCTGGAGCAC
                                                              / BstXI 2170      2180      2190      2200      2210      2220
       CTGAAGGAACTGATACTCGACCTGCAGTCTAGATAGgtaatctctgcttaaaagcacaga
        ░░░░░░░░ L  D  L  Q  S  R  *
                           / /
                        Pstl Xbal
```

ANTIBODY PRODUCTION METHOD

SEQUENCE LISTING

The instant application contains a Sequence Listing which has been submitted electronically in ASCII format and is hereby incorporated by reference in its entirety. Said ASCII copy, created on Oct. 30, 2013, is named P44483_SL.txt and is 44,184 bytes in size.

TECHNICAL FIELD

The invention relates to an antibody production method. More specifically, the invention relates to an antibody production method that includes administering an antigen to a fish bearing water vesicles, and allowing the fish to produce an antibody.

BACKGROUND ART

A technique that allows *Escherichia coli*, yeast, or the like to produce a useful protein by utilizing genetic recombination technologies, and a technique that administers such a protein to a mouse or the like as an antigen, and allows the mouse or the like to produce an antibody, are widely used at present.

However, a protein produced by a prokaryote such as *Escherichia coli* has not been accurately subjected to multimer formation and posttranslational modification such as glycosylation. A protein produced by yeast has not been subjected to complete posttranslational modification, and may not have the original functions.

In order to solve the above problem, a technique that allows insect cells or mammalian cells (e.g., mouse, pig, or human) to produce a useful protein has been used. However, this technique has problems in that a considerable cost is required to culture the cells, and it takes time to obtain a useful protein.

In view of the above situation, use of fish as a bioreactor has recently attracted attention. This technique has an advantage in that a protein derived from fish is subjected to multimer formation and posttranslational modification such as glycosylation in the same manner as a protein derived from a mammal. Patent Document 1 discloses a technique that allows a transgenic fish to produce a glycoprotein multimer by utilizing the above advantage, and collects the glycoprotein multimer from the embryo, larva, fry, tissue, or blood.

Fish can be raised relatively easily and inexpensively. It is very easy to care for fish since egg laying/collection can be controlled by controlling the water temperature, feeding, the duration of sunshine, the water quality, and the like.

The inventors of the invention developed various techniques such as a technique that produces an antigen-producing yeast, and administers the yeast to a fish (e.g., zebrafish) as feed to allow the fish to produce a specific antibody derived from the fish, and a technique that allows a fish to produce an antibody to a membrane protein such as a G protein-coupled receptor (GPCR) (that has been considered to be difficult) (Japanese Patent Application No. 2009-83900) (see Patent Documents 2 and 3, for example).

However, since these techniques collect the antibody from the whole body of the fish, it is impossible to repeatedly obtain the antibody produced by the fish while keeping the fish alive.

In order to solve the above problem, the inventors focused on fish bearing water vesicles (e.g., Bubble Eye) in the course of the development of the invention. Such goldfish are widely grown in Japan and overseas for ornamental purpose.

Patent Document 4 discloses that the blister fluid of a Bubble Eye has a function of protecting fish cells or promoting cell proliferation, and makes it possible to efficiently process fish cells in a state in which the quality of unfertilized eggs is maintained, for example.

However, Patent Document 4 does not even suggest allowing the blister fluid to produce a useful protein (e.g., antibody), and no attempts have been made to utilize a fish bearing water vesicles for production of an antibody.

RELATED-ART DOCUMENT

Patent Document

Patent Document 1: JP-A-2001-86992
Patent Document 2: JP-A-2007-255892
Patent Document 3: JP-A-2009-73783
Patent Document 4: JP-A-2009-183151

SUMMARY OF THE INVENTION

Technical Problem

An object of the invention is to provide an antibody production method that can repeatedly obtain an antibody produced by a fish while keeping the fish alive.

Solution to Problem

The inventors conducted extensive studies in order to achieve the above object. As a result, the inventors found that it is possible to repeatedly obtain an antibody produced by a fish while keeping the fish alive by administering an antigen to a fish bearing water vesicles (e.g., Bubble Eye). This finding has led to the completion of the invention.

Specifically, several aspects of the invention relate to the following antibody production method, an antibody produced by the antibody production method, and the like (see (1) to (8)).

(1) An antibody production method including administering an antigen to a fish bearing water vesicles, and allowing the fish to produce an antibody.
(2) The antibody production method according to (1), wherein the antigen is administered to the water vesicle.
(3) The antibody production method according to (1) or (2), wherein the antigen is administered together with an oil base, or administered together with an oil base and inactivated *Escherichia coli* cells.
(4) The antibody production method according to any one of (1) to (3), further including collecting the antibody produced by the fish from the water vesicle of the fish.
(5) The antibody production method according to any one of (1) to (4), wherein the fish bearing water vesicles is a Bubble Eye or a Ranchu.
(6) The antibody production method according to any one of (1) to (5), wherein the antigen is a protein or a glycoprotein.
(7) The antibody production method according to (6), wherein the antigen is enhanced green fluorescent protein (EGFP), glucoamylase, or leucine-rich repeat-containing G protein-coupled receptor 3 (LGR3).
(8) An antibody produced by the antibody production method according to any one of (1) to (7).

Advantageous Effects of the Invention

The antibody production method according to the aspect of the invention makes it possible to allow a fish to produce an antibody, and repeatedly obtain a large amount of antibody while keeping the fish alive. The antibody production method according to the aspect of the invention can produce a useful antibody even when using a glycoprotein or the like as the antigen.

BRIEF DESCRIPTION OF DRAWINGS

FIG. 1 is a view showing Western blotting results (Example 1).

FIG. 6 is a view showing antigen-antibody reaction results (the purified GA-His and the culture supernatant of GA-His) (Example 1).

FIG. 7 is a view illustrating the sequence of pCold-TF-hLGR3 (Example 2). FIG. 7 discloses SEQ ID NOS 24-25, respectively, in order of appearance.

DESCRIPTION OF EMBODIMENTS

Figure 2:
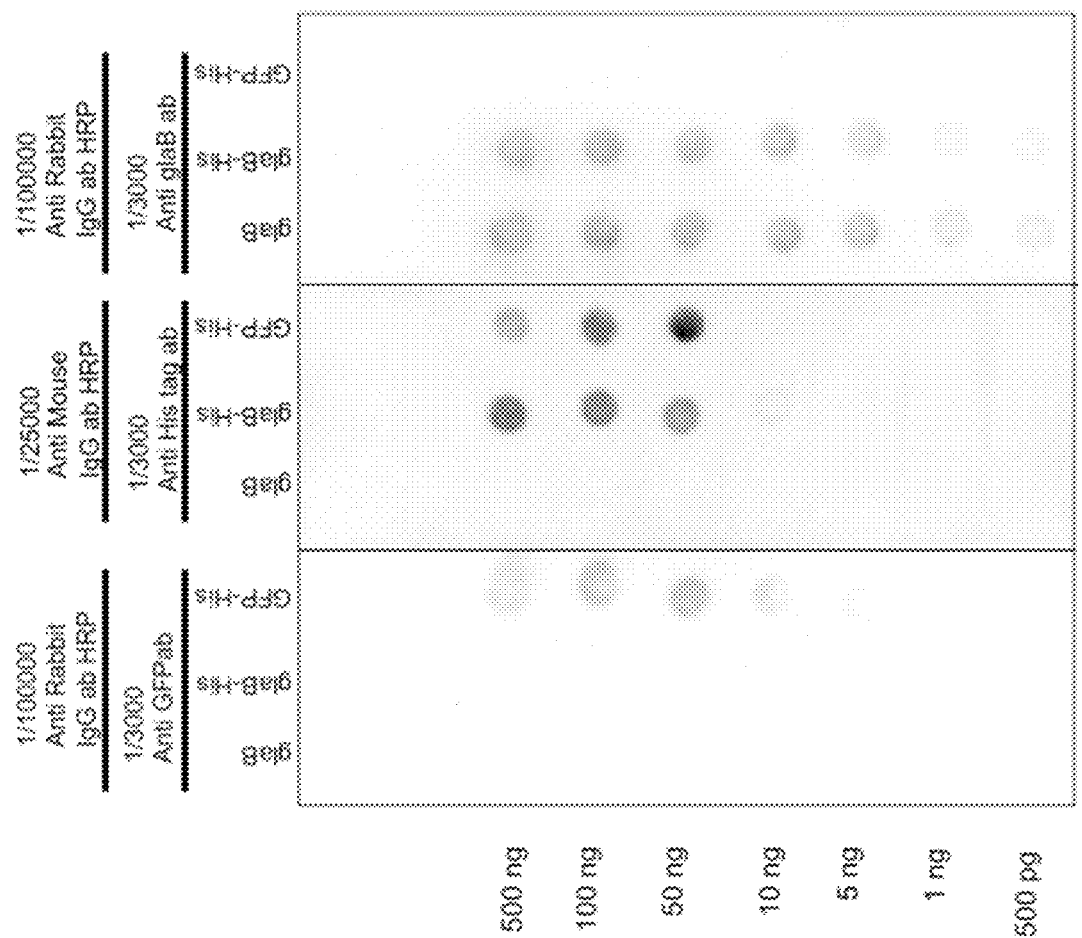
FIG. 2 is a view showing dot blotting results (Example 1).

The term "antibody production method" used herein in connection with the embodiments of the invention refers to a method that is targeted at a fish as a living organism that produces an antibody, and includes administering an antigen to a fish, and allowing the fish to produce an antibody.

More specifically, the term "antibody production method" used herein in connection with the embodiments of the invention refers to a method that includes administering an antigen to a fish bearing water vesicles, and allowing the fish to produce an antibody. The antibody production method may further include an additional known step or method that is used when producing an antibody.

The antigen may be administered by an arbitrary method as long as it is possible to allow a fish to produce an antibody. For example, a protein, yeast, or the like that serves as the antigen may be orally administered as feed, or the antigen may be administered directly to the abdominal cavity or the water vesicle via injection or the like. It is particularly preferable to administer the antigen directly to the water vesicle.

The antigen may be administered independently, or may be administered together with an adjuvant. The adjuvant is not particularly limited as long as it is possible to assist the fish in producing an antibody. It is particularly preferable to use an oil base, or a combination of an oil base and inactivated *Escherichia coli* cells, as the adjuvant.

The antibody production method according to the embodiments of the invention may further include collecting the antibody produced by the fish. It is preferable to collect the antibody while keeping the fish alive. It is particularly preferable to collect the blister fluid including the antibody from the water vesicle of the fish, for example. In this case, the antibody produced by the fish can be collected while keeping the fish alive by inserting a syringe needle or the like directly into the water vesicle of the fish, and collecting the blister fluid.

The term "fish bearing water vesicles" used herein in connection with the embodiments of the invention refers to an arbitrary fish of which the skin forms a water vesicle. The water vesicle of the fish bearing water vesicles contains lymph that includes the antibody produced by the fish. When the lymph has been collected from the water vesicle using a syringe or the like, the water vesicle is filled with lymph again. Examples of the fish bearing water vesicles include goldfish such as the Bubble Eye and the Ranchu.

The antigen used in connection with the embodiments of the invention is not particularly limited as long as the fish can produce an antibody. Examples of the antigen include transmembrane proteins such as GPCR and LGR3, soluble proteins such as EGFP, and glycoproteins such as α-dystroglycan and glucoamylase.

The amount of the antigen administered to the fish is not particularly limited as long as the fish can produce an antibody. It is particularly preferable to administer the antigen (protein) in an amount of 100 μg or more.

The invention is further described below by way of examples. Note that the invention is not limited to the following examples.

Example 1

I. Preparation of Antigen

Antigen: *Aspergillus oryzae* Glucoamylase
1-1. Construction of Plasmid
1) Incorporation of Nitrate Reductase Gene Derived from *Aspergillus oryzae* (Hereinafter May be Referred to as "niaD Gene") into *Escherichia coli* Vector A primer A (SEQ ID NO: 1), a primer B (SEQ ID NO: 2), and an LA-Taq polymerase (Takara Holdings Inc.) were mixed, and subjected to PCR under the following conditions using genomic DNA derived from *Aspergillus oryzae* as a template to amplify the niaD gene (SEQ ID NO: 3).

The genomic DNA derived from *Aspergillus oryzae* was prepared according to the method described in Reference 1.
Reference 1: R. C. Garber and O. C. Yoder, Anal. Biochem., 135, 416-422 (1983) PCR conditions
1 cycle at 96° C. (5 min)
30 cycles at 96° C. (20 sec), 60° C. (30 sec), and 72° C. (5 min)
1 cycle at 72° C. (7 min)

The resulting PCR amplified product was treated with restriction enzymes (PstI-HindIII) (37° C.), and the PstI-HindIII fragment of the niaD gene was separated by agarose gel electrophoresis. A QIAquick Gel Extraction Kit (QIAGEN) was used for separation.

The PstI-HindIII fragment of the niaD gene was ligated to the PstI-HindIII site of *Escherichia coli* plasmid pUC119 (Takara Holdings Inc.) using a DNA Ligation Kit Ver. 1 (Takara Holdings Inc.), and transformed into the *Escherichia coli* JM109 strain to obtain *Escherichia coli* plasmid pNIA2 into which the niaD marker gene was subcloned.

The *Escherichia coli* plasmid pNIA2 can be introduced into both the PstI site and the SaiI site as a unique site.
2) Incorporation of Glucoamylase B Terminator Gene Derived from *Aspergillus Oryzae* (Hereinafter May be Referred to as "glaB Terminator Gene") into *Escherichia coli* Vector A primer C (SEQ ID NO: 4), a primer C (SEQ ID NO: 5), and an LA-Taq polymerase (Takara Holdings Inc.) were mixed, and subjected to PCR under the following conditions using genomic DNA derived from *Aspergillus oryzae* as a template to amplify the glaB terminator gene (SEQ ID NO: 6).

PCR Conditions
1 cycle at 96° C. (5 min)
30 cycles at 96° C. (20 sec), 60° C. (30 sec), and 72° C. (5 min)
1 cycle at 72° C. (7 min)

The resulting PCR amplified product was treated with restriction enzymes (SalI-XhoI) (37° C.), and the SalI-XhoI fragment of the glaB terminator gene was separated by agarose gel electrophoresis. A QIAquick Gel Extraction Kit (QIAGEN) was used for separation.

The SalI-XhoI fragment of the glaB terminator gene was ligated to the SalI site of the *Escherichia coli* plasmid pNIA2 obtained in section 1) using a DNA Ligation Kit Ver. 1 (Takara Holdings Inc.), and transformed into the *Escherichia coli* JM109 strain to obtain *Escherichia coli* plasmid pNIAT into which the glaB terminator gene was subcloned.

The *Escherichia coli* plasmid pNIAT can be introduced into both the PstI site and the SalI site as a unique site.

3) Incorporation of sodM Promoter Gene Derived from *Aspergillus oryzae* (Hereinafter May be Referred to as "sodM Promoter Gene")

A primer E (SEQ ID NO: 7), a primer F (SEQ ID NO: 8), and an LA-Taq polymerase (Takara Holdings Inc.) were mixed, and subjected to PCR under the following conditions using genomic DNA derived from *Aspergillus oryzae* as a template to amplify the sodM promoter gene (SEQ ID NO: 9).
PCR Conditions
1 cycle at 96° C. (5 min)
30 cycles at 96° C. (20 sec), 60° C. (30 sec), and 72° C. (5 min)
1 cycle at 72° C. (7 min)

The resulting PCR amplified product was treated with restriction enzymes (SalI-PstI) (37° C.), and the SalI-PstI fragment of the sodM promoter gene was separated by agarose gel electrophoresis. A QIAquick Gel Extraction Kit (QIAGEN) was used for separation.

The SalI-PstI fragment of the sodM promoter gene was ligated to the PstI-SalI site of the *Escherichia coli* plasmid pNIAT obtained in section 2) using a DNA Ligation Kit Ver. 1 (Takara Holdings Inc.), and transformed into the *Escherichia coli* JM109 strain to obtain *Escherichia coli* plasmid pNMB into which the sodM promoter gene was subcloned.

A gene that encodes the expression target protein using *Aspergillus oryzae* can be introduced into the SaiI site as a unique site using the *Escherichia coli* plasmid pNMB.

1-2. Incorporation of Target Gene
1) Preparation of Vector

The *Escherichia coli* plasmid pNMB constructed in section 1-1 was treated with a restriction enzyme (SaiI) (37° C.). After the addition of a dNTP so that the final concentration was 10 mM, the mixture was treated with a T4 DNA polymerase (Takara Holdings Inc.) for 1 hour (37° C.). The mixture was then treated with alkaline phosphatase derived from bacteria (Takara Holdings Inc.) for 30 minutes (50° C.). The resulting product was eluted using a PCR clean-up column (Promega KK) to obtain a vector.

2) Preparation of Insert

An insert subcloned into the vector was prepared using a gene that encodes the expression target protein using *Aspergillus oryzae* as the target gene.

The target gene was a) the glucoamylase B (glaB) gene derived from *Aspergillus oryzae* (SEQ ID NO: 10 (amino acid sequence: SEQ ID NO: 11)), orb) the glucoamylase B (glaB) gene derived from *Aspergillus oryzae* to which an His-tag gene was bound (SEQ ID NO: 12 (amino acid sequence: SEQ ID NO: 13)).

A sense primer (30 bp downstream from the start codon of the target gene) (5'-terminal was phosphorylated) (SEQ ID NO: 14), an antisense primer (49 bp upstream from the stop codon of the target gene) (5'-terminal was phosphorylated) (SEQ ID NO: 15), and a Pfu Taq polymerase (Toyobo Co., Ltd.) were mixed, and subjected to PCR under the following conditions using genomic DNA derived from *Aspergillus oryzae* (see section 1-1.1)) as a template to amplify the target gene.

The resulting PCR amplified product was eluted using a PCR clean-up column (Promega KK) to obtain an insert.
PCR Conditions
1 cycle at 96° C. (5 min)
30 cycles at 96° C. (20 sec), 60° C. (30 sec), and 72° C. (5 min)
1 cycle at 72° C. (7 min)

3) Ligation of Vector and Insert

The vector obtained in section 1) and the insert of each target gene obtained in section 2) were mixed in a molar ratio of 1:20, subjected to ligation using a DNA Ligation Kit Ver. 1 (Takara Holdings Inc.), and transformed into the *Escherichia coli* JM109 strain.

A transformant in which the reading frame of each target gene was subcloned in the forward direction with respect to the sodM promoter was used as a target gene expression plasmid.

1-3. Acquisition of Target Gene Expression Strain

The NiaD variant of *Aspergillus oryzae* (deposited at International Patent Organism Depositary (IPOD), National Institute of Advanced Industrial Science and Technology (accession number: FERMP-17707)) was transformed by a PEG-calcium method using the target gene expression plasmid prepared in section 1-2.

1) The PEG-calcium method was performed as described below in accordance with Reference 2.

About $10^8$ spores of *Aspergillus oryzae* were inoculated onto a DPY liquid medium (100 ml), and cultured at 28° C. for 18 to 20 hours. After germination, glass beads (diameter: 0.6 cm) were added to the culture flask, followed by shaking at 30° C. and 130 rpm for 24 hours.

The hyphae were collected, and washed 2 to 3 times with a 0.8 M NaCl aqueous solution. After the addition of 10 ml of a fresh protoplasting solution (15 mg/ml Yatalase (Takara Bio Inc.), 10 mg/ml Cellulase Onozuka R-10 (Yakult Honsha), 0.8 M NaCl, 10 mM phosphate buffer (pH: 6.0), and 1 mM DTT), the mixture was slowly shaken at 30° C. for 3 to 4 hours to effect cell wall digestion to prepare protoplasts.

The resulting protoplast solution was filtered using a filter "Miracloth" (Calbiochem), and the filtrate was centrifuged (2500×g) at 4° C. for 5 minutes to collect the protoplasts.

The protoplasts were washed with an ice-cooled solution 1 (0.8 M NaCl, 10 mM $CaCl_2$, and 10 mM Tris-HCl (pH: 8.0)), and suspended in the solution 1 ($2\times10^8$/ml). After the addition of a solution 2 (40% PEG4000, 50 mM $CaCl_2$, 10 mM Tris-HCl (pH: 8.0)) (0.2 vol), the mixture was slowly mixed.

0.1 ml of the protoplast solution was put in a tube (15 ml). After the addition of 15 μl or less (3 to 7 μg) of the target DNA, the mixture was allowed to stand on ice for 30 minutes. After the addition of 0.5 ml of the solution 2, the mixture was slowly stirred, and allowed to stand at room temperature or 20 minutes. After the addition of 5 ml of the solution 1, the mixture was stirred, and centrifuged (2500×g) at 4° C. for 5 minutes.

A precipitate including the protoplasts was suspended in 0.1 nil of the solution 1, and the suspension was spread over a CD regeneration medium containing 0.8 M NaCl. After the addition of a CD soft agar medium cooled to 30° C., the medium was solidified, and the mixture was cultured at 28° C. for 4 to 7 days.

Reference 2: Mol Gen Genet, 218, 99-104, (1989)

2) A transformant that can be grown using a Czapek-Dox medium (2% glucose, 0.1% dipotassium hydrogen phosphate, 0.05% potassium chloride, 0.05% magnesium sulfate, 0.001% iron sulfate, and 0.3% sodium nitrate) that uses nitric acid as a single nitrogen source was selected to obtain a plurality of transformants including the target gene expression plasmid.

1-4. Preparation of Target Gene Product

The transformants obtained in section 1-3 were cultured using a potato dextrose medium to form spores, and the spores were collected using sterilized water.

The collected spores were inoculated onto a GPY liquid medium (2% glucose, 1% polypeptone, 0.5% yeast extract, 0.1% dipotassium hydrogen phosphate, 0.05% potassium chloride, 0.05% magnesium sulfate, 0.001% iron sulfate, and 0.3% sodium nitrate) (100 ml) in a 500 ml Erlenmeyer flask so that the final spore concentration was $1 \times 10^6$/ml.

The spores were cultured at 30° C. for 3 days, and a culture supernatant in which the target gene product was secreted and expressed was collected.

1-5. Concentration of Culture Supernatant

Part of the culture supernatant collected in section 1-4 was centrifuged (3000×g) using a filter unit "Centriprep 10" (Millipore, molecular weight cut-off: 10,000 NMWL), and concentrated.

1-6. Determination of GA Concentration in Culture Supernatant

The GA concentration in the culture supernatant collected in section 1-4 was estimated by separating the proteins from the culture supernatant by SDS-PAGE, and quantifying the CBB stained image using image analysis software "CS Analyzer 3.0" (ATTO).

Specifically, the following steps 1) to 5) were performed.
1) Purified GA obtained in 1-7 was dissolved in PBS (3 to 11 µg) (standard).

A 5× sample buffer (2.5 M Tris-HCl, 10% glycerol, 0.05% bromophenol blue, and 10% SDS) was respectively added to the purified GA solution and the 1× culture supernatant (1 to 3 µl) (final concentration: 1×), and the mixtures were boiled at 100° C. for 5 minutes to obtain samples.
2) Proteins were separated from the samples by SDS-PAGE (7.5% polyacrylamide gel, 200 V, 20 m A).
3) The gel was immersed in a CBB staining solution (0.25% CBB-R250, 50% methanol, and 5% acetic acid), and shaken at room temperature for 30 minutes to stain the proteins.
4) The gel was immersed in a destaining solution (25% methanol and 10% acetic acid), and shaken at room temperature to wash CBB that was not bound to the proteins.
5) The gel was photographed using a CCD camera (Light Capture II, ATTO), the detected band of the GA was quantified by zone densitometry analysis (CS Analyzer 3.0), and a calibration curve was drawn from the integrated value of purified GA.

The GA concentration in the culture supernatant (unconcentrated) estimated from the calibration curve was about 3.0 µg/µl.

The GA concentration in the culture supernatant that was 5-fold concentrated in section 1-5 was adjusted to 4 µg/µl based on the above result using a goldfish Ringer's solution (125 mM NaCl, 2.6 mM KCl, 10 mM 2-[4-(2-hydroxyethyl)-1-piperazinyl]ethanesulfonic acid (HEPES) (pH: 7.4)) (hereinafter may be referred to as "the culture supernatant of GA" or "the culture supernatant of GA-His").

1-7. Purification of Target Gene Product
1) Target Gene Product

Ammonium sulfate (saturation concentration: 70%) was added to part of the culture supernatant collected in section 1-4, and the mixture was stirred at 4° C. overnight to precipitate proteins. The precipitate was removed by centrifugation.

After the addition of a resin "Toyopearl Butyl-650M" (Tosoh Corporation) to the culture supernatant, the mixture was stirred at a low temperature overnight, and the resin was collected.

The collected resin was washed twice with a 1.5 M ammonium sulfate solution, and the target GA protein was eluted using a 10 mM acetate buffer (pH: 5.0), and freeze-dried to obtain purified GA protein.

The GA concentration in purified GA protein was adjusted to 4 µg/µl using a goldfish Ringer's solution (hereinafter may be referred to as "purified GA").

2) His-Tagged Target Gene Product

The culture supernatant including the target gene product (see section 1-4) was added to a nickel column (His GraviTrap column (GE Healthcare)), and recombinant glucoamylase bound to the column was eluted using a 20 mM sodium phosphate buffer (pH: 7.4) including 0.5 M NaCl and 400 mM imidazole.

The eluated fraction was transferred to a dialysis membrane, and dialyzed twice (4° C., 3 hours) using a buffer (1 l) including a 50 mM sodium acetate buffer (pH: 5.0) to purify the His-tagged target gene product.

The concentrated GA in the purified His-tagged target gene product was adjusted to 4 µg/µl using a goldfish Ringer's solution (hereinafter may be referred to as "purified GA-His").

Antigen: EGFP-his Protein 2-1. Preparation of Vector (Construction of Plasmid to Incorporation of Target Gene)

A vector "pCold TF DNA" (Takara Bio Inc.) was modified as described below to prepare a pColdTEE-EGFP-His vector that was a construct in which a 5'-untranslated region, a translation enhancing element (TEE), an EGFP, and a His-tag (purification tag) DNA sequence (3'-terminal) were arranged downstream of a CspA promoter.

1) A primer G (SEQ ID NO: 18), a primer H (SEQ ID NO: 19), and a PCR Enzyme "TAKARA Ex Taq" (Takara Bio Inc.) were mixed, and subjected to PCR under the following conditions using a pXI-EGFP vector (prepared by incorporating EGFP (SEQ ID NO: 17) downstream of pXI (SEQ ID NO: 16) (see Japanese Patent Application No. 2009-107344 and Reference 3)) as a template to amplify a fragment in which the start codon of the egfp gene was converted into a restriction enzyme (SmaI) recognition sequence, and the 3'-terminal was converted into a His-tag DNA sequence.

Reference 3: Johnson A D, Krieg P A. pXeX, a vector for efficient expression of cloned sequences in Xenopus embryos. Gene. 1994 September PCR Conditions
1 cycle at 95° C. (1 min)
30 cycles at 95° C. (10 sec), 55° C. (30 sec), and 72° C. (2 min)
1 cycle at 72° C. (5 min)

2) A primer G (SEQ ID NO: 18), a primer I (SEQ ID NO 20), and a PCR Enzyme "TAKARA Ex Taq" (Takara Bio Inc.) were mixed, and subjected to PCR under the above conditions (see section 1)) using the amplified product obtained in section 1) (i.e., a fragment in which the start codon of the egfp gene was converted into a restriction enzyme (SmaI) recognition sequence, and the 3'-terminal was converted into a His-tag DNA sequence as a template to amplify an egfp-his6 gene ("his6" disclosed as SEQ ID NO: 26) fragment in which a restriction enzyme (SfiI) recognition sequence was arranged downstream of the His-tag.

3) A primer J (SEQ ID NO: 21), a primer K (SEQ ID NO: 22), and a PCR Enzyme "TAKARA Ex Taq" (Takara Bio Inc.) were mixed, and subjected to PCR under the following conditions using a vector "pCold TF DNA" (Takara Bio Inc.) as a template to amplify a DNA fragment in which a restriction enzyme (SmaI) recognition sequence was bound to the TEE, and a restriction enzyme (SfiI) recognition sequence was arranged upstream of the transcription terminator sequence.

The DNA fragment amplified in section 3) and the egfp-his6 gene ("his6" disclosed as SEQ ID NO: 26) fragment digested by the restriction enzymes SmaI and SfiI (see section 2)) were subjected to ligation using the DNA Ligation Kit Mighty Mix (Takara Bio inc.) to prepare a pColdTEE-EGFP-His vector.

2-2. Preparation of Target Gene Product

The pColdTEE-EGFP-His vector prepared in section 2-1 was transformed into *Escherichia coli* BL21, smeared on an LB plate medium containing ampicillin sodium (final concentration: 50 μg/ml), and cultured at 37° C. overnight. Note that a product manufactured by Wako Pure Chemical Industries, Ltd. was used as the reagent unless otherwise indicated.

1) The resulting colony was inoculated onto an LB-ampicillin liquid medium, and cultured at 37° C. for 12 hours with shaking. The culture supernatant was inoculated onto a 2×YT-ampicillin liquid medium (50 μg/ml ampicillin sodium, 1.6% Bacto Trypton (BD), 1% dry yeast extract (Nacalai Tesque, Inc.), and 0.5% NaCl (pH: 7.0)), and cultured at 37° C. with shaking until the absorbance at a wavelength of 600 nm reached 0.4 to 0.5.

After allowing the culture supernatant to stand at 15° C. for 30 minutes, 0.1 mM isopropyl β-D-1-thiogalactopyranoside (IPTG) was added in an amount of 1/1000 of that of the culture supernatant, and expression of the EGFP-His protein was induced at 15° C. for 24 hours with shaking.

After confirming expression of the EGFP-His protein with the naked eye, the mixture was centrifuged (3000×g) at 4° C. for 15 minutes to collect fungus bodies. The fungus bodies were washed twice with a cooled 1× phosphate buffered saline (PBS) (137 mM NaCl, 2.7 mM KCl, 1.5 mM $KH_2PO_4$, and 8.1 mM $Na_2HPO_4$) to remove residual medium components.

2) After the addition of 40 ml of an Ni column elution buffer A (20 mM sodium phosphate, 0.5 M NaCl, and 20 mM imidazol (pH: 7.4)), the fungus bodies were crushed using an ultrasonic cell disrupter (MICROSON XL 2000 (MISONIX)).

The mixture was then centrifuged (12,000×g) at 4° C. for 30 minutes to collect a supernatant, and impurities were removed using a filter having a pore size of 0.20 μm (ADVANTEC) to prepare an *Escherichia coli-expressed* protein extract.

The *Escherichia coli-expressed* protein extract was added to an Ni column (GE healthcare) charged with an Ni Sepharose medium (GE healthcare) using a peristaltic pump (BioRad) to bind the EGFP-His protein to the medium.

3) An EGFP-His protein was eluted from the column using the Ni column elution buffer A (20 mM sodium phosphate, 0.5 M NaCl, and 20 mM imidazol (pH: 7.4)) and the Ni column elution buffer B (20 mM sodium phosphate, 0.5 M NaCl, and 500 mM imidazol (pH: 7.4)) by utilizing the continuous concentration gradient of imidazol (20 to 500 mM).

4) The Ni column elution buffer contained in the EGFP-His protein fraction was replaced with a DEAE column elution buffer A (20 mM 2-amino-2-(hydroxymethyl)propane-1,3-diol (Tris)-HCl (pH: 8.0)) using an ultrafiltration membrane (Millipore) to prepare a sample. The sample was added to an anion-exchange column changed with a DEAE Sepharose Fast Flow medium (GE healthcare) using a low-pressure chromatography system (AKTAprime plus (GE healthcare)) to bind EGFP-His protein to the medium, and EGFP-His protein was eluted using the DEAE column elution buffer A (20 mM Tris-HCl (pH: 8.0)) and a DEAE column elution buffer B (20 mM Tris-HCl, 1 M NaCl (pH: 8.0)) by utilizing the continuous concentration gradient of NaCl (0 to 1 M).

5) The solvent contained in the fraction including EGFP-His protein eluted from the column (see section 4)) was replaced with a divalent ion-free goldfish Ringer's solution (125 mM NaCl, 2.6 mM KCl, 10 mM 2-[4-(2-hydroxyethyl)-1-piperazinyl]ethanesulfonic acid (HEPES) (pH: 7.4)) so that an EGFP-His protein concentration was 4 μg/μl.

II. Determination of Antigen-Antibody Reaction

The antigens (purified GA, purified GA-His, and EGFP-His proteins) prepared in section I were allowed to react with an antibody, and the presence or absence of an antigen-antibody reaction was determined by Western blotting or dot blotting.

1. Antibody
1) Anti-his Antibody
Anti-His Antibody (Amersham Biosciences)
2) Anti-GlaB Antibody A peptide (SEQ ID NO: 11) of a fall-length glucoamylase protein was designed, and synthesized by chemosynthesis. A rabbit was immunized with the peptide (antigen) conjugated to keyhole limpet hemocyanin (KLH) as a carrier protein to obtain an antibody (custom antibody production (Invitrogen)).

2. Western Blotting

1) A 5× sample buffer (2.5 M Tris, 10% glycerol, 0.05% bromophenol blue, and 10% SDS) was respectively added to EGFP-His protein, purified GA, and purified GA-His prepared in section I (final concentration: 1×), and the mixtures were boiled at 100° C. for 5 minutes to obtain samples.

The samples were subjected to electrophoresis (10% polyacrylamide gel, 200 V, 20 mA) to separate the proteins.

2) The proteins were transferred to a PVDF membrane (ATTO) using a semi-dry blotter, and the PVDF membrane was rinsed twice with 0.5% Tween20/PBS (0.5% PBST), for 1 hour with shaking to block the PVDF membrane.

The PVDF membrane was thus blocked and rinsed twice with PBST, washed once with 0.5% PBST for 15 minutes, and washed twice with 0.5% PBST for 5 minutes to remove extra blocking reagents.

3) The anti-His antibody and the anti-GlaB antibody (see section 1) were diluted (1/3000 and 1/1000, respectively) with a Can Get Signal (TOYOBO) solution 1. The PVDF membrane was immersed therein, and reacted at room temperature for 1 hour with shaking. The PVDF membrane was then washed three times with 0.5% PBST for 10 minutes to remove extra antibody solution.

4) An anti-mouse IgG HRP labeled secondary antibody and an anti-rabbit IgG HRP labeled secondary antibody were diluted (1/25,000 and 1/100,000, respectively) with a Can Get Signal Solution 2. The PVDF membrane was immersed therein, and reacted at room temperature for 1 hour with shaking.

5) The PVDF membrane was then washed three times with PBST for 10 minutes, immersed in an Amersham ECL plus Western Blotting Detection Reagent (GE healthcare), reacted at room temperature for 5 minutes, photographed using a CCD camera (Light Capture (ATTO)), and luminescence was detected using a CS Analyzer 3.0 (ATTO).

As shown in FIG. 1 (see (A) (i.e., the PVDF membrane reacted with the anti-His antibody)), an EGFP-His protein (EGFP-His in FIG. 1) and purified GA-His (glaB-His in FIG. 1) were detected from the PVDF membrane reacted with the anti-His antibody.

As shown in FIG. 1 (see (B) (i.e., the PVDF membrane reacted with the anti-GlaB antibody)), purified GA (glaB in FIG. 1) and purified GA-His (glaB-His in FIG. 1) were detected from the PVDF membrane reacted with the anti-GlaB antibody.

It was confirmed from the above results that purified GA-His can be detected using the anti-GlaB antibody and the anti-His antibody.

In FIG. 1, the amount of the sample in each lane, the primary antibody, the secondary antibody, and the dilution ratio are shown in the upper part of each photograph (M: Prestained SDS-PAGE Standards (Broad Range) (BioRad)).

2. Dot Blotting

1) An EGFP-His protein, purified GA, and purified GA-His prepared in section I were respectively diluted with PBS (range: 250 μg/μl to 250 ng/μl) to obtain the samples.
2) A PVDF membrane was immersed in methanol for 5 minutes with shaking, immersed in ultrapure water twice for 10 minutes with shaking, and immersed in PBS for 10 minutes or more with shaking to equilibrate the PVDF membrane.
3) The PVDF membrane was sandwiched between the sheets of Elleair Prowipe (DAIO PAPER Co.) immediately before the dropwise addition of the sample to remove unnecessary PBS. The sample (2 μl) was added dropwise to the PVDF membrane placed on a Parafilm, and the PVDF membrane was air-dried.
4) The PVDF membrane was dried and then equilibrated and blocked with 5% skimmed milk/0.05% Tween 20 in TBS (20 mM Tris-HCl and 150 mM NaCl, pH: 7.5) (0.05% TBST).
5) The PVDF membrane was rinsed twice with 0.05% TBST, washed for 10 minutes with shaking, and washed twice for 5 minutes with shaking to remove unnecessary skimmed milk solution.
6) The anti-His antibody, an anti-GFP antibody (MBL), and the anti-GlaB antibody (see section 1) were respectively diluted (1/3000) with a Can Get Signal solution 1. The PVDF membrane was immersed therein, and reacted at room temperature for 2 hours with shaking.

The PVDF membrane was then washed three times with 0.05% TBST for 10 minutes to remove unnecessary antibody solution.

7) An anti-mouse IgG HRP labeled secondary antibody and an anti-rabbit IgG HRP labeled secondary antibody were diluted (1/25,000 and 1/100,000, respectively) with a Can Get Signal solution 2. The PVDF membrane was immersed therein, and reacted at room temperature for 1 hour with shaking.
8) The PVDF membrane was washed three times with 0.05% TBST for 10 minutes, reacted with an Amersham ECL plus Western Blotting Detection Reagent, and luminescence was detected in the same manner as in the case of using Western blotting.

As shown in FIG. 2 (left), when detecting the EGFP-His protein, the purified GA, and the purified GA-His using the anti-GFP antibody, a reaction was observed in the spots of EGFP-His protein (GFP-His in FIG. 2) from 10 to 500 ng.

As shown in FIG. 2 (center), when detecting the EGFP-His protein, the purified GA, and the purified GA-His using the anti-His antibody, a reaction was observed in the spots of purified GA-His (glaB-His in FIG. 2) from 10 to 500 ng, and the spots of EGFP-His protein (GFP-His in FIG. 2) from 50 to 500 ng.

As shown in FIG. 2 (right), when detecting the EGFP-His protein, the purified GA, and the purified GA-His using the anti-GlaB antibody, a reaction was observed in the spots of purified GA (glaB in FIG. 2) and the spots of purified GA-His (glaB-His in FIG. 2) from 500 μg to 500 ng.

It was confirmed from the above results that purified GA-His can be detected using the anti-GlaB antibody and the anti-His antibody.

It was also confirmed that 500 pg or more of the purified GA and the purified GA-His can be detected using the 1/1000-fold diluted anti-GlaB antibody, 10 ng or more of the purified GA-His and 50 ng or more of the EGFP-His protein can be detected using the 1/3000-fold diluted anti-His antibody, and 10 ng or more of the EGFP-His protein can be detected using the 1/3000-fold diluted anti-GFP antibody.

In FIG. 2, the type of proteins added dropwise to each lane, the primary antibody, the secondary antibody, and the dilution ratio are shown in the upper part of each photograph. The amount of protein added dropwise to each lane is shown on the left side of the photographs.

III. Production of Antibody by Fish Bearing Water Vesicles

1. Sample

1) Fish Bearing Water Vesicles

Figure 3:
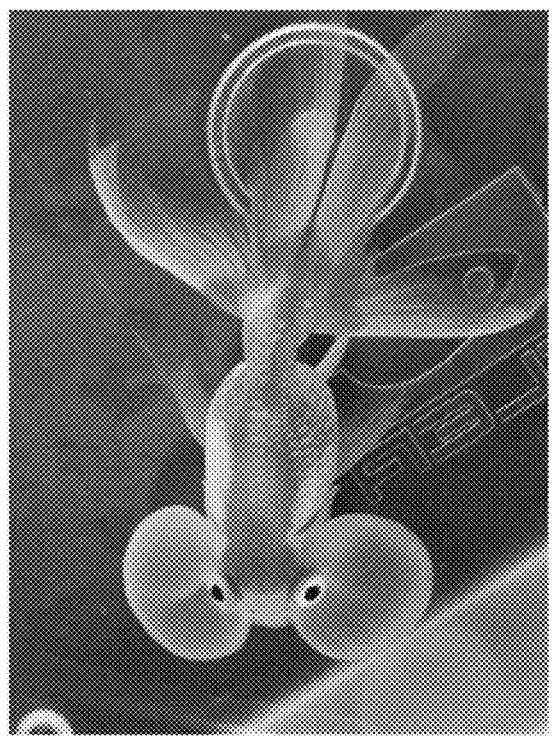
FIG. 3 is a view illustrating a photograph of a Bubble Eye (Example 1).

Bubble Eyes purchased from Maruteru. Fish Farm (Yatomi-shi, Aichi Prefecture) were used as fish bearing water vesicles. The Bubble Eyes were kept in tap water (water temperature: 20 to 25° C.) in which the residual chlorine was neutralized by adding a neutralizer for goldfish/killifish (Nichido Co., Ltd.). FIG. 3 illustrates a photograph of one of the Bubble Eyes used.

2) Reagent

A product manufactured by Wako Pure Chemical Industries, Ltd. was used as the reagent unless otherwise indicated.

3) Antigen

The EGFP-His protein, the purified GA-His, or the culture supernatant of GA-His prepared in section I was used as an antigen.

4) Adjuvant

The following adjuvants (A) to (D) were prepared, and used.
(A) Oil base including a lecithin
(B) Oil base including inactivated *Mycobacterium tuberculosis* cells
(C) Oil base including inactivated *Aspergillus oryzae* cells
(D) Oil base including inactivated *Escherichia coli* cells (1) Preparation of Oil Base The oil base was prepared as described below by modifying the method described in Reference 4.

Specifically, 0.1 g of egg-yolk lecithin was added to 10 g of glycerol, and the mixture was stirred at 60° C. using a stirrer. After the gradual addition of 10 g of arachis oil (Nacalai Tesque, Inc.), the mixture was stirred until a homogenous mixture was obtained to prepare an oil base.

Reference 4: J. A. REYNOLDS et al. 1980 (Adjuvant activity of a novel metabolizable lipid emulsion with inactivated viral vaccines. Reynolds J A, Harrington D Q Crabbs C L, Peters C J, Di Luzio N R. Infect Immun. 1980 June; 28 (3): 937-943.

(2) Preparation of Inactivated *Escherichia coli* Cells and Inactivated *Aspergillus oryzae* Cells The *Escherichia coli* DH5α strain was inoculated onto an LB medium, and cultured at 37° C. for 16 hours with shaking.

The *Aspergillus oryzae* OSI-1013 strain was inoculated onto a DPY liquid medium, and cultured at 28° C. for 18 to 20 hours.

The bacteria were crushed using a sonicator to obtain inactivated *Escherichia coli* cells and inactivated *Aspergillus oryzae* cells.

(3) Inactivated *Mycobacterium tuberculosis* Cells

*Mycobacterium tuberculosis* H37 Ra (dry, Difco Laboratories) was used as inactivated *Mycobacterium tuberculosis* cells.

(4) Mixing of Oil Base with Inactivated *Escherichia coli* Cells, Inactivated *Mycobacterium Tuberculosis* Cells, or Inactivated *Aspergillus oryzae* Cells Inactivated *Escherichia coli* cells, inactivated *Mycobacterium tuberculosis* cells, or inactivated *Aspergillus oryzae* cells was added to the oil base in an amount of 0.5 mg/ml.

(5) Mixing of Antigen with Adjuvant

Each of the adjuvants (A) to (D) and the antigen solution were mixed in a volume ratio of 1:1 using a syringe (volume: 1 ml) (Terumo Corporation) and a 18G reagent mixing needle (Sansyo Co., Ltd.) to prepare a water-in-oil emulsion. The water-in-oil emulsion was used for immunization. The adjuvant including the cells was used only for initial immunization, and only the oil base was subsequently used as the adjuvant.

2. Production of Antibody

Experimental groups A to E in which the EGFP-His protein was used as the antigen, experimental groups F to J in which the purified GA-His was used as the antigen, experimental groups K and L in which the culture supernatant of GA-His was used as the antigen, and a control experimental group M were provided. Six Bubble Eyes were used for each experimental group. Table 1 shows the combination of the antigen and the adjuvant in each experimental group.

Figure 4:
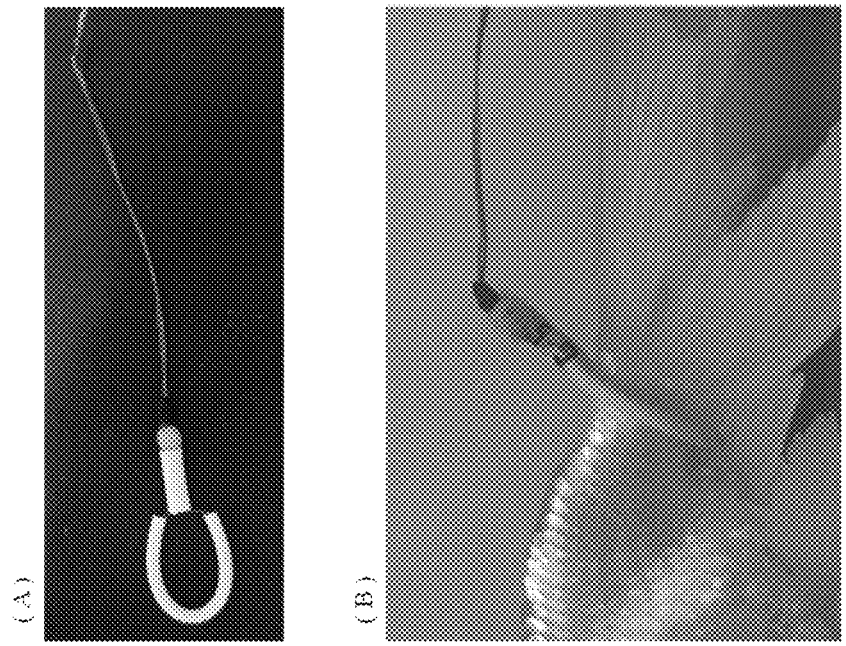
FIG. 4 is a view illustrating a photograph of a tag (Example 1).

36 Bubble Eyes used for the experimental groups A to E (in which the EGFP-His protein was used as the antigen) and the control experimental group M were individually kept in a fish tank (61) (identical water system). 36 Bubble Eyes used for the experimental groups F to J (in which the purified GA-His was used as the antigen) and the experimental groups K and L (in which the culture supernatant of GA-His was used as the antigen) were provided with an identification tag ((A) in FIG. 4) on their peduncle ((B) in FIG. 4), and kept in a fish tank (601) on an experimental group basis (i.e., six Bubble Eyes per fish tank).

Each Bubble Eye was immunized by injecting only the antigen, or an emulsion prepared by mixing the antigen and the adjuvant, into the right water vesicle in an amount of 100 µg. Each Bubble Eye was immunized every 14 days over 70 days.

50 to 100 µl of the blister fluid was collected from the left water vesicle of each Bubble Eye before immunization and on the day of immunization. When collecting the blister fluid on the day of immunization, the blister fluid was collected after immunization.

The collected blister fluid was centrifuged (1500×g) at 4° C. for 10 minutes to collect a supernatant, which was used as an antibody titer measurement sample. Note that the sample was stored at −20° C. until the sample was used to detect an antigen-specific antibody.

TABLE 1

| Experimental group | Antigen | Adjuvant |
|---|---|---|
| A | EGFP-His protein | No |
| B | | Oil base |
| C | | Oil base + inactivated *Escherichia coli* |
| D | | Oil base + inactivated *Mycobacterium tuberculosis* |

TABLE 1-continued

| Experimental group | Antigen | Adjuvant |
|---|---|---|
| E | | Oil base + inactivated *Aspergillus oryzae* |
| F | Purified GA-His | No |
| G | | Oil base |
| H | | Oil base + inactivated *Escherichia coli* |
| I | | Oil base + inactivated *Mycobacterium tuberculosis* |
| J | | Oil base + inactivated *Aspergillus oryzae* |
| K | Culture supernatant of GA-His | No |
| L | | Oil base |
| M | No (only goldfish Ringer's solution) | Oil base |

3. Antibody Detection by Dot Blotting

1) Sample

The blister fluid collected in section 2 was defrosted, and centrifuged (10,000×g) at 4° C. for 10 minutes to remove a precipitate to obtain a sample.

An anti-myc tag antibody (SANTACRUZ) was used as a negative control, and an anti-His antibody (Amersham Biosciences) that was 1/100 to 1/5000-fold diluted with PBS was used as a positive control.

2) Antigen

The EGFP-His protein and the purified GA-His prepared in section I, of which the solvent was replaced with PBS, were used as the antigen.

3) Dot Blotting

An antigen-antibody reaction was detected by dot blotting using a sandwich technique (see (1) to (6)).

(1) A PVDF membrane (ATTO) was immersed in methanol for 5 minutes with shaking, immersed in ultrapure water twice for 10 minutes with shaking, and immersed in PBS for 10 minutes or more with shaking to equilibrate the PVDF membrane. The PVDF membrane was sandwiched between sheets of Elleair Prowipe (DAIO PAPER Co.) immediately before the dropwise addition of the sample to remove unnecessary PBS. The sample (2 µl) was added dropwise to the PVDF membrane placed on a Parafilm, and the PVDF membrane was air-dried.

(2) The dried PVDF membrane was equilibrated and blocked with 5% skimmed milk/0.05% Tween 20 in TBS (20 mM Tris-HCl and 150 mM NaCl (pH: 7.5)) (0.05% TBST).

The PVDF membrane was then rinsed twice with 0.05% TBST, washed for 10 minutes with shaking, and washed twice for 5 minutes with shaking to remove unnecessary skimmed milk solution.

(3) EGFP-His protein or the purified GA-His (antigen) was diluted to 5 or 10 ng/µl with a Can Get Signal (TOYOBO) solution 1. The PVDF membrane was immersed therein, and reacted at room temperature for 2 hours with shaking. The PVDF membrane was then washed three times with 0.05% TBST for 10 minutes to remove unnecessary antigen solution.

(4) An anti-GFP antibody (MBL) or an anti-GA antibody (provided by Gekkeikan Sake Co., Ltd.) was diluted (1/3000) with a Can Get Signal solution 1. The PVDF membrane was immersed therein, and reacted at room temperature for 1 hour with shaking. The PVDF membrane was then washed three times with 0.05% TBST for 10 minutes to remove unnecessary antibody solution.

(5) An anti-rabbit IgG HRP labeled secondary antibody was diluted (1/100,000) with a Can Get Signal solution 2. The PVDF membrane was immersed therein, and reacted at room temperature for 1 hour with shaking. The PVDF membrane was then washed three times with 0.05% TBST for 10 minutes to remove unnecessary antibody solution.

(6) The PVDF membrane was then washed three times with PBST for 10 minutes, immersed in an Amersham ECL plus Western Blotting Detection Reagent (GE healthcare), and reacted at room temperature for 5 minutes, and luminescence was detected using a CCD camera.

Figure 5:
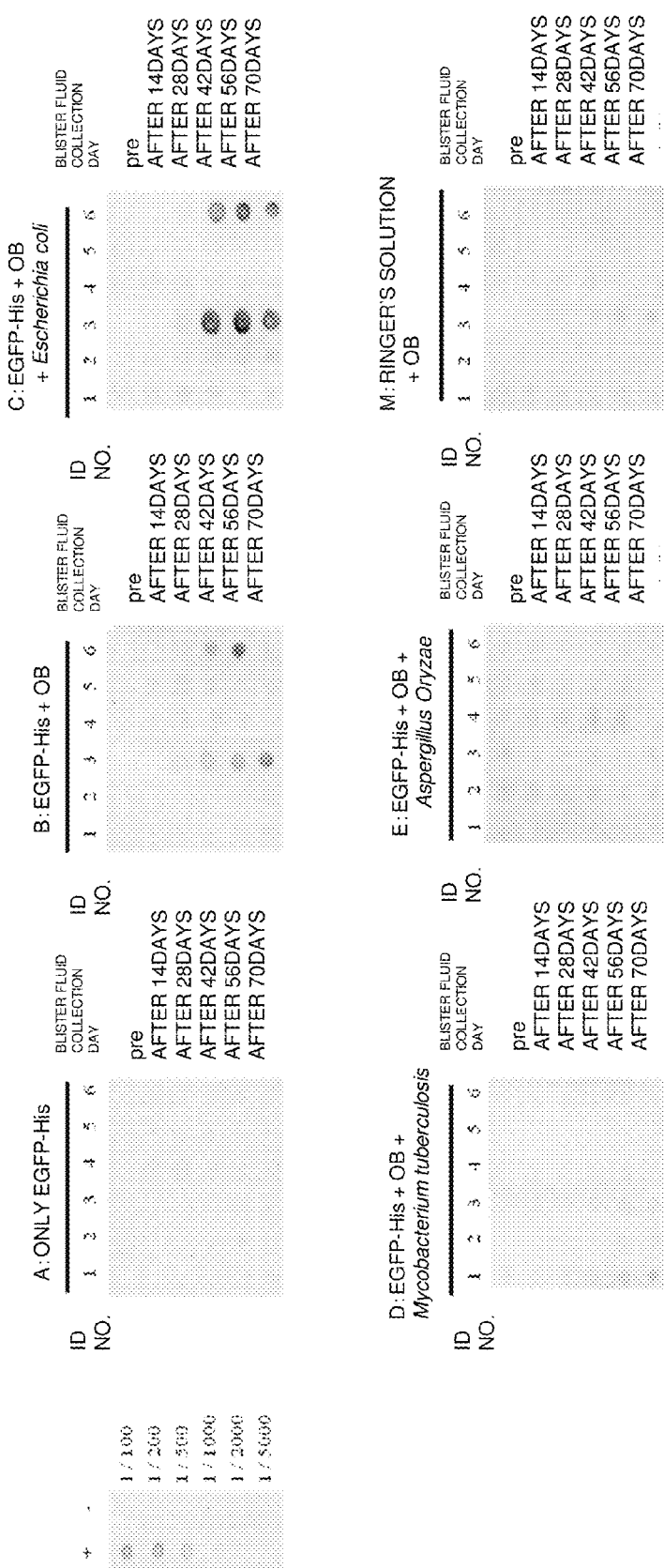
FIG. 5 is a view showing antigen-antibody reaction results (EGFP-His protein) Example 1).
Figure 6:
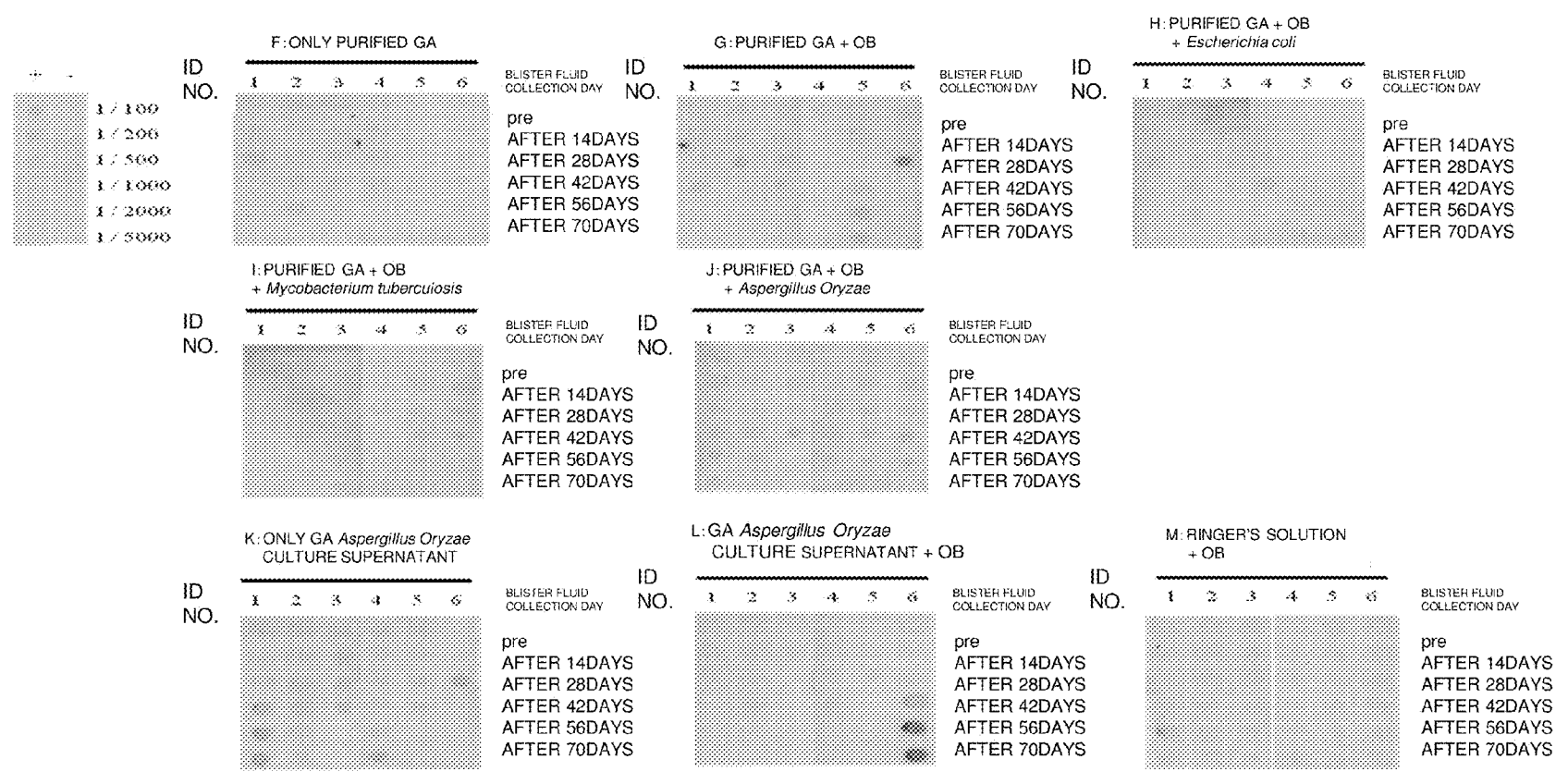

FIG. 5 and Table 2 show the results for the experimental groups in which the EGFP-His protein was administered, and FIG. 6 and Table 3 show the results for the experimental groups in which the purified GA-His or the culture supernatant of GA-His was administered.

TABLE 2

|   |   | pre | After 14 days | After 28 days | After 42 days | After 56 days | After 70 days |
|---|---|---|---|---|---|---|---|
| A | 1 | − | − | − | − | − | − |
|   | 2 | − | − | − | − | − | − |
|   | 3 | − | − | − | − | − | − |
|   | 4 | − | − | − | − | − | − |
|   | 5 | − | − | − | − | − | − |
|   | 6 | − | − | − | − | − | − |
| B | 1 | − | − | − | − | − | − |
|   | 2 | − | − | − | − | − | − |
|   | 3 | − | − | − | + | + | + |
|   | 4 | − | − | − | − | − | − |
|   | 5 | − | − | − | − | − | − |
|   | 6 | − | − | − | + | + | − |
| C | 1 | − | − | − | − | − | − |
|   | 2 | − | − | − | − | − | − |
|   | 3 | − | − | − | + | + | + |
|   | 4 | − | − | − | − | − | − |
|   | 5 | − | − | − | − | − | − |
|   | 6 | − | − | − | + | + | + |
| D | 1 | − | − | − | − | − | − |
|   | 2 | − | − | − | − | − | − |
|   | 3 | − | − | − | − | − | − |
|   | 4 | − | − | − | − | − | − |
|   | 5 | − | − | − | − | − | − |
|   | 6 | − | − | − | − | − | − |
| E | 1 | − | − | − | − | − | − |
|   | 2 | − | − | − | − | − | − |
|   | 3 | − | − | − | − | − | − |
|   | 4 | − | − | − | − | − | − |
|   | 5 | − | − | − | − | − | − |
|   | 6 | − | − | − | − | − | − |
| M | 1 | − | − | − | − | − | − |
|   | 2 | − | − | − | − | − | − |
|   | 3 | − | − | − | − | − | − |
|   | 4 | − | − | − | − | − | − |
|   | 5 | − | − | − | − | − | − |
|   | 6 | − | − | − | − | − | − |

As shown in FIG. 5 and Table 2, an antibody to the EGFP-His protein (EGFP-His in FIG. 5 (hereinafter the same)) was detected, and an increase in antibody titer was observed in two Bubble Eyes in the experimental group B in which the oil base was administered as the adjuvant together with the antigen, and two Bubble Eyes in the experimental group C in which the oil base including inactivated *Escherichia coli* cells was administered together with the antigen.

In contrast, an increase in antibody titer with respect to the EGFP-His protein was not observed in the Bubble Eyes in the experimental group D in which the oil base including *Mycobacterium tuberculosis* cells was administered together with the antigen and the Bubble Eyes in the experimental group E in which the oil base including *Aspergillus oryzae* cells was administered together with the antigen. An increase in antibody titer was also not observed in the Bubble Eyes in the experimental group A in which only the antigen was administered.

Bubble Eye No. 3 in the experimental group B that showed an increase in antibody titer with respect to EGFP-His protein indicated an increase in an antibody titer in the blister fluid when 42 days had elapsed after the first immunization. In particular, the antibody titer gradually increased from the 56th day to the 70th day after the first immunization. Bubble Eye No. 6 showed a slight increase in antibody titer when 42 days had elapsed after the first immunization, and the antibody titer further increased when 56 days had elapsed after the first immunization.

Bubble Eye No. 3 in the experimental group C that showed an increase in antibody titer with respect to EGFP-His protein indicated a significant increase in antibody titer when 42 days had elapsed after the first immunization. Bubble Eye No. 6 showed an increase in antibody titer from the 42nd day to the 70th day after the first immunization.

Note that FIG. 5 also shows the results for the positive control (+) in which the anti-His antibody was reacted, and the results for the negative control (−) in which the anti-myctag antibody was reacted (upper left) (dilution ratio: 1/100 to 1/5000).

In FIG. 5, the alphabetical character shown above each PVDF membrane indicates the experimental group, the numerals (1 to 6) shown above each PVDF membrane indicate the identification numbers of the Bubble Eyes, and the immunization conditions (OB: oil base) for each experimental group are shown on the right of the alphabetical character. The sample (blister fluid) collection day (i.e., the number of days elapsed after the first immunization) ("pre" indicates before immunization) is shown on the right of each PVDF membrane.

TABLE 3

|   |   | pre | After 14 days | After 28 days | After 42 days | After 56 days | After 70 days |
|---|---|---|---|---|---|---|---|
| F | 1 | − | − | − | − | − | − |
|   | 2 | − | − | − | − | − | − |
|   | 3 | − | − | − | − | − | − |
|   | 4 | − | − | − | − | − | − |
|   | 5 | − | − | − | − | − | − |
|   | 6 | − | − | − | − | − | − |
| G | 1 | − | − | − | − | − | − |
|   | 2 | − | − | + | − | − | − |
|   | 3 | − | − | − | − | − | − |
|   | 4 | − | − | − | − | − | − |
|   | 5 | − | − | − | − | + | + |
|   | 6 | − | − | + | − | − | − |
| H | 1 | − | − | − | − | − | − |
|   | 2 | − | − | − | − | − | − |
|   | 3 | − | − | − | − | − | − |
|   | 4 | − | − | − | − | − | − |
|   | 5 | − | − | − | − | − | − |
|   | 6 | − | − | − | − | − | − |
| I | 1 | − | − | − | − | − | − |
|   | 2 | − | − | − | − | − | − |
|   | 3 | − | − | − | − | − | − |
|   | 4 | − | − | − | − | − | − |
|   | 5 | − | − | − | − | − | − |
|   | 6 | − | − | − | − | − | − |
| J | 1 | − | − | − | − | − | − |
|   | 2 | − | − | − | − | − | − |
|   | 3 | − | − | − | − | − | − |
|   | 4 | − | − | − | − | − | − |
|   | 5 | − | − | − | − | − | − |
|   | 6 | − | − | − | − | − | − |
| K | 1 | − | − | − | + | + | + |
|   | 2 | − | − | − | − | − | − |
|   | 3 | − | − | − | − | − | − |

TABLE 3-continued

| | | pre | After 14 days | After 28 days | After 42 days | After 56 days | After 70 days |
|---|---|---|---|---|---|---|---|
| | 4 | − | − | − | − | − | + |
| | 5 | − | − | − | − | | |
| | 6 | − | − | + | | | |
| L | 1 | − | − | − | − | | |
| | 2 | − | − | − | − | | |
| | 3 | − | − | | | | |
| | 4 | − | − | − | − | | |
| | 5 | − | − | − | | | |
| | 6 | − | − | − | + | + | + |
| M | 1 | − | − | − | − | − | − |
| | 2 | − | − | − | − | − | − |
| | 3 | − | − | − | − | − | − |
| | 4 | − | − | − | − | − | − |
| | 5 | − | − | − | − | − | − |
| | 6 | − | − | − | − | − | − |

As shown in FIG. 6 and Table 3, an antibody to the EGFP-His protein was detected, and an increase in antibody titer was observed in three Bubble Eyes in the experimental group G in which the oil base was administered as the adjuvant together with the antigen.

In contrast, an increase in antibody titer with respect to the purified GA-His was not observed in Bubble Eyes in the experimental group H in which the oil base including inactivated *Escherichia coli* cells was administered together with the antigen, the Bubble Eyes in the experimental group I in which the oil base including inactivated *Mycobacterium tuberculosis* cells was administered together with the antigen, and the Bubble Eyes in the experimental group J in which the oil base including inactivated *Aspergillus oryzae* cells was administered together with the antigen. An increase in antibody titer was also not observed in the Bubble Eyes in the experimental group F in which only the antigen was administered.

An increase in antibody titer with respect to the culture supernatant of GA-His (GA *Aspergillus oryzae* culture supernatant in FIG. 6 (hereinafter the same)) was observed in three Bubble Eyes in the experimental group K in which only the antigen was administered, and one Bubble Eye in the experimental group L in which the oil base was administered together with the antigen.

Bubble Eye No. 1 in the experimental group K that showed an increase in antibody titer with respect to culture supernatant GA-His showed an increase in antibody titer when 42 days had elapsed after the first immunization. An increase in antibody titer was observed from the 42nd day to the 70th day after the first immunization.

Bubble Eye No. 4 showed a slight increase in antibody titer when 70 days had elapsed after the first immunization, and Bubble Eye No. 6 showed an increase in antibody titer when 28 days had elapsed after the first immunization. Bubble Eye No. 6 in the experimental group L that showed an increase in antibody titer with respect to the culture supernatant of GA-His, showed a slight increase in antibody titer when 42 days had elapsed after the first immunization, and the antibody titer further increased when 56 days had elapsed after the first immunization. An increase in antibody titer was observed from the 42nd day to the 70th day after the first immunization.

The Bubble Eyes in the control experimental group M in which the oil base was administered together with the goldfish Ringer's solution, did not show an increase in antibody titer with respect to the EGFP-His protein, the purified GA-His, and the culture supernatant of GA-His.

Note that FIG. 6 also shows the results for the positive control (+) in which the anti-His antibody was reacted, and the results for the negative control (−) in which the anti-myctag antibody was reacted (upper left) (dilution ratio: 1/100 to 1/5000).

In FIG. 6, the alphabetical character shown above each PVDF membrane indicates the experimental group, the numerals (1 to 6) shown above each PVDF membrane indicate the identification numbers of the Bubble Eyes, and the immunization conditions (OB: oil base) for each experimental group are shown on the right of the alphabetical character. The sample (blister fluid) collection day (i.e., the number of days elapsed after the first immunization) ("pre" refers to "before immunization") is shown on the right of each PVDF membrane.

Example 2

I. Preparation of Antigen

Antigen: LGR3
1-1. Preparation of Vector (Construction of Plasmid to Incorporation of Target Gene)

A vector "pCold TF DNA" (Takara Bio Inc.) was modified as described below to prepare an expression vector "pCold-TEE-His-hLGR3-LRR". In order to remove the trigger factor (TF) sequence of the vector "pCold TF DNA" (Takara Bio Inc.), PCR was performed using primers having a restriction enzyme (SuraI or SfiI) recognition sequence utilizing the vector "pCold TF DNA" as a template to amplify the vector.

Likewise, PCR was performed using primers having a restriction enzyme (SmaI or SfiI) recognition sequence utilizing a vector "pCR4-TOPO-hLGR3" (Invitrogen) as a template to amplify the leucine-rich region (LRR) (SEQ ID NO: 23) of a human leucine-rich repeat-containing G protein-coupled receptor 3 (hLGR3) gene (see the hLGR marker part in FIG. 7 (base: 1695 to 2173)).

The amplified product was purified, and treated with a restriction enzyme, and an expression vector "pCold-TEE-His-hLGR3-LRR" was constructed using a DNA Ligation Kit (Takara Bio Inc.). A construct was prepared using *Escherichia coli* HST08 strain, and the base sequence of the expression vector "pCold-TEE-His-hLGR3-LRR" was determined. The base sequence completely coincided with the expected base sequence. It was confirmed from the above result that the construct was properly obtained.

II. Determination of Antigen-Antibody Reaction

The construct (expression vector "pCold-TEE-His-hLGR3-LRR") prepared in section I was transformed into the *Escherichia coli* Origami strain.

The strain for which transformation was confirmed by direct PCR was inoculated onto an LB medium (5 ml) (to which ampicillin was added so that the final concentration was 100 μg/ml), and pre-cultured at 37° C. and 180 rpm for 6 hours.

1 ml of the preculture solution was inoculated onto a 2×YT medium (250 ml), cultured at 37° C. and 130 rpm until $OD_{600}$-0.45 to 0.5 was reached, then promptly cooled to 15° C., and kept for 30 minutes. After the addition of IPTG so that the final concentration was 0.1 mM, the mixture was cultured at 15° C. and 130 rpm for 24 hours.

The cells were collected, suspended in a 20 mM phosphate buffer (pH: 7.4, 20 mM imidazole and 1.5 M NaCl), subjected to sonication, and centrifuged (20,000×g) at 4° C. for 30 minutes.

The supernatant was collected as a soluble fraction, and the precipitate was prepared as a solubilized insoluble fraction using 6 M urea. Each fraction was purified using an Ni Sepharose column, and concentrated (Amicon Ultra (Millipore)), and the degree of purification was determined by SDS-PAGE.

Figure 8:
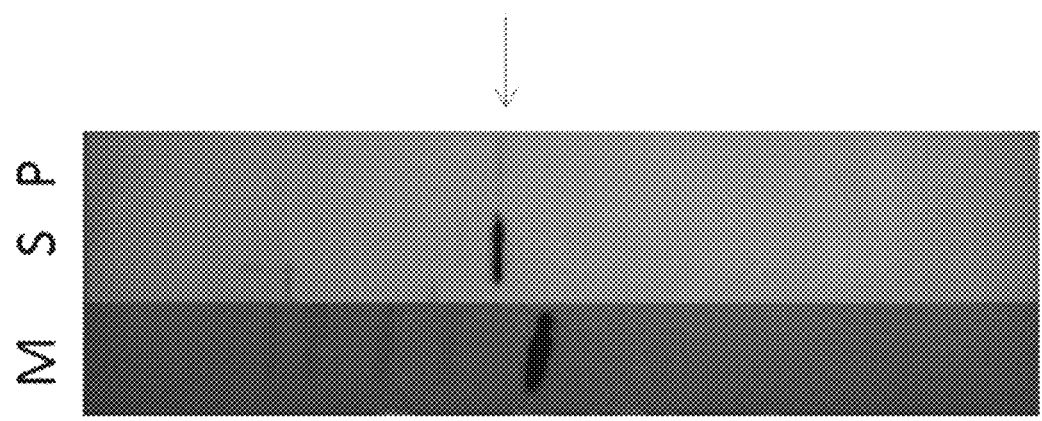
FIG. 8 is a view showing antigen-antibody reaction results (Example 2).

The purified and concentrated soluble fraction and solubilized insoluble fraction were separated by SDS-PAGE, and detected using an anti-His antibody (Amersham Biosciences). As shown in FIG. 8, a band was detected in the soluble fraction and the solubilized insoluble fraction at the target molecular weight position (see the arrow in FIG. 8). It was thus confirmed that LRR of the target hLGR3 protein was expressed. In FIG. 8, M indicates the marker, S indicates the soluble fraction, and P indicates the solubilized insoluble fraction.

III. Production of Antibody by Fish Bearing Water Vesicles

1. Sample

Five healthy Bubble Eyes (length: about 8 to 10 cm) were purchased, and kept for 2 months or more in the same manner as in Example 1, and the same reagents as those used in Example 1 were used as samples.

The soluble fraction (LRR of hLGR3 protein) (0.6 μg/pi) and the insoluble fraction (LRR of hLGR3 protein) (0.1 μg/μl) prepared in section II were used as antigens. An oil base prepared by homogenously mixing the components shown in Table 4 was used as an adjuvant.

TABLE 4

| Oil base | |
| --- | --- |
| Component | Amount (g) |
| Glycerol | 10.0 |
| Lecithin | 0.1 |
| Peanut oil | 10.0 |

2. Production of Antibody

An antibody was produced by the following steps (1) to (5).
(1) 100 μl of the blister fluid was collected from each Bubble Eye before immunization.
(2) An emulsion prepared by mixing 90 μl of the antigen (soluble fraction (0.6 μg/μl)) prepared in section II with 90 μl of the oil base was injected into the water vesicle of each Bubble Eye.
(3) 100 μl of the blister fluid was collected from each Bubble Eye when 1 week had elapsed after the first immunization (see (2)), and an emulsion prepared by mixing 100 μl of the antigen (solubilized insoluble fraction (0.1 μg/μl)) prepared in section II with 100 μl of the oil base was immediately injected into the water vesicle of each Bubble Eye.
(4) 100 μl of the blister fluid was collected from each Bubble Eye when 1 week had elapsed after the second immunization (see (3)) (second sampling).
(5) 100 μl of the blister fluid was collected from each Bubble Eye when 1 week had elapsed after the second sampling (see (4)) (third sampling).

The collected blister fluid was centrifuged (1500×g) at 4° C. for 10 minutes to collect a supernatant, which was used as an antibody titer measurement sample. The sample was stored at 4° C. until the sample was used to detect an antigen-specific antibody. Note that no Bubble Eye died during the immunization period.

3. Antibody Detection by Dot Blotting
1) Sample

The blister fluid collected from each Bubble Eye (see section 1) was diluted (dilution ratio: 1/2, 1/10, 1/20, 1/100, 1/200, 1/1000, or 1/2000) to obtain samples.

An anti-His antibody was used as a detection primary antibody, an anti-TF antibody (GenScript) was used as a positive control, and an anti-AIF antibody (rabbit polyclonal antibody) (PromoKine) was used as a negative control.

2) Antigen

His-TF-hLGR3 (see FIG. 7, base: 278 to 295, Trigger Factor (base: 296 to 1657), and hLGR marker (base: 1695 to 2173)) that was prepared in the same manner as in sections I and II and adjusted to a final concentration of 5 ng/μl using PBS, was used as an antigen.

3) Dot Blotting

An antigen-antibody reaction was detected by dot blotting using a sandwich technique (see Example 1).

Figure 9:
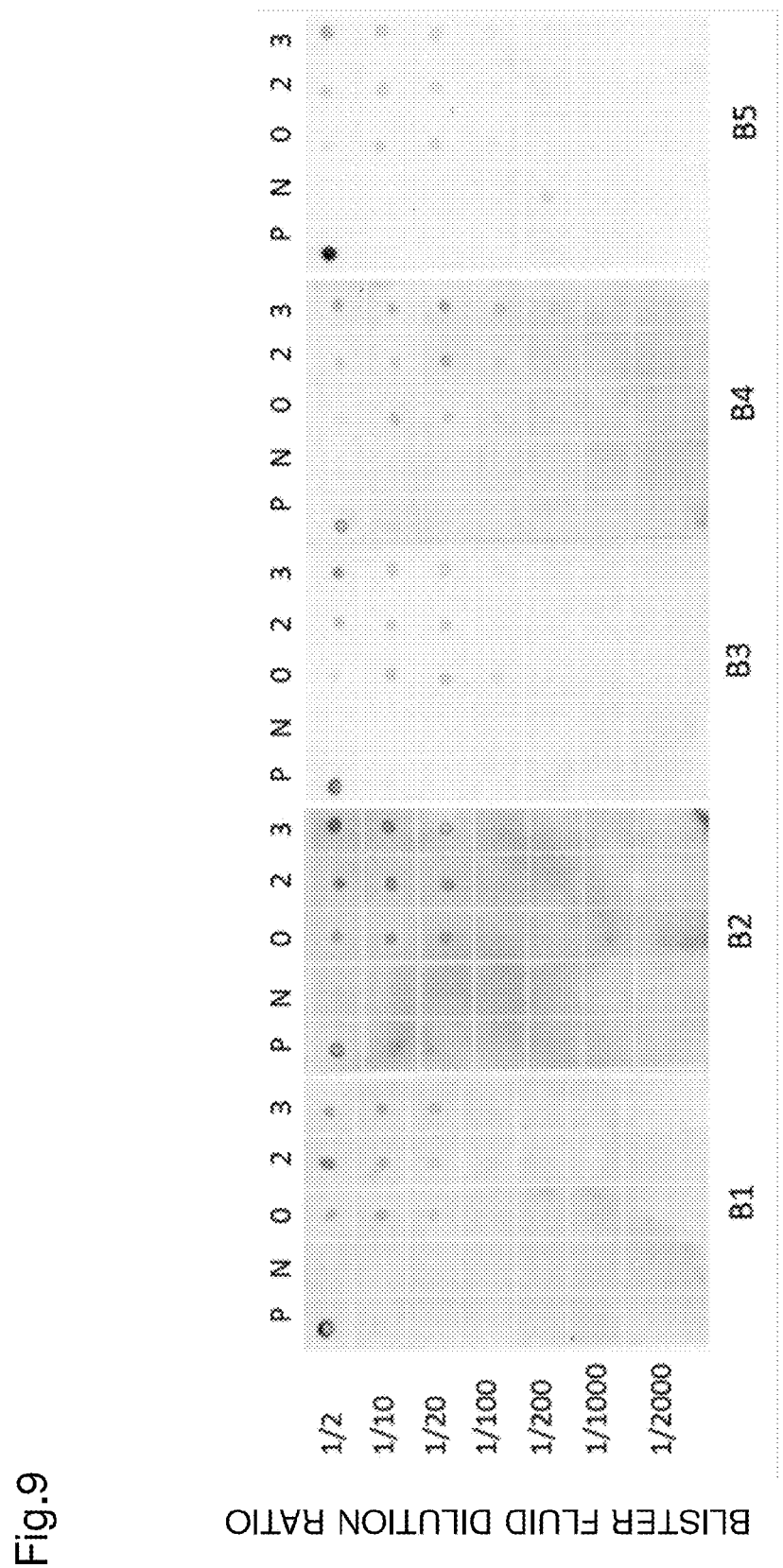
FIG. 9 is a view showing antigen-antibody reaction results (Example 2).

The sample (2 μl) prepared in section 1) was added dropwise to a PVDF membrane (see FIG. 9). The PVDF membrane was reacted with the antigen (see 2)), and then reacted with the detection primary antibody, the negative control, or the positive control (see 1)). An anti-mouse IgG HRP labeled secondary antibody (Cell Signaling) was diluted (1/25,000), and reacted with the PVDF membrane.

After completion of the reaction, the PVDF membrane was washed, immersed in an Amersham ECL plus Western Blotting Detection Reagent (GE healthcare), and reacted at room temperature for 5 minutes, and luminescence was detected using a CCD camera.

As shown in FIG. 9, when using the anti-His antibody as the detection primary antibody, the sample prepared by 1/2-fold diluting the blister fluid showed an increase in signal (before immunization<second sampling<third sampling). The above results suggest that an antibody to the antigen was produced in the blister fluid as a result of administering the antigen to the Bubble Eye.

In FIG. 9, reference signs B1 to B5 indicate the Bubble Eyes from which each sample is derived. "0" indicates the blister fluid before immunization, "2" indicates the blister fluid collected by the second sampling, and "3" indicates the blister fluid collected by the third sampling. The blister fluid dilution ratio (1/2 to 1/2000) is shown on the left. "P" indicates the positive control, and "N" indicates the negative control. Each control was diluted in a dilution ratio of 1/100, 1/200, 1/500, 1/1000, 1/2000, and 1/5000, and solid-phased.

It was confirmed from the above results that it is possible to produce an antibody using a fish bearing water vesicles. It was also confirmed that an antigen can be administered directly to the water vesicle of a fish bearing water vesicles, and the antibody produced by the fish can be collected directly from the water vesicle.

Since 1 to 5 ml of lymph can be collected directly from the water vesicle at one time, it is possible to collect a large amount of antibody produced by a single antigen administration. Since the lymph including the antibody could be collected while keeping the Bubble Eye alive, it was possible to repeatedly collect the lymph including the antibody from the Bubble Eye.

INDUSTRIAL APPLICABILITY

According to the embodiments of the invention, it is possible to repeatedly obtain a large amount of antibody produced by a fish while keeping the fish alive. The antibody according to the embodiments of the invention may be an antibody to a glycoprotein or the like, and may be widely used in the same manner as an antibody intended for mammals and the like.

---

The invention claimed is:

1. An antibody production method comprising administering an antigen together with an oil base to a fish bearing water vesicles, and allowing the fish to produce an antibody.

2. The antibody production method according to claim 1, wherein the antigen is administered to the water vesicle.

3. The antibody production method according to claim 1, wherein the antigen is administered together with an oil base and inactivated *Escherichia coli* cells.

4. The antibody production method according to claim 1, further comprising collecting the antibody produced by the fish from the water vesicle of the fish.

5. The antibody production method according to claim 1, wherein the fish bearing water vesicles is a Bubble Eye or a Ranchu.

6. The antibody production method according to claim 1, wherein the antigen is a protein or a glycoprotein.

7. The antibody production method according to claim 6, wherein the antigen is enhanced green fluorescent protein (EGFP), glucoamylase, or leucine-rich repeat-containing G protein-coupled receptor 3 (LGR3).

* * * * *

SEQUENCE LISTING

```
<160> NUMBER OF SEQ ID NOS: 26

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aactgcagaa caggccccaa attcaattaa ttgca                               35

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cccaagcttt ggatttccta cgtcttcaat acaaacc                             37

<210> SEQ ID NO 3
<211> LENGTH: 5140
<212> TYPE: DNA
<213> ORGANISM: Aspergillus oryza

<400> SEQUENCE: 3
ctgcagaaca ggccccaaat tcaattaatt gcacctgtta ttattagtct tactacaagt     60
ttgcatatcg gcatctcaat aaaaaccgc atactacgaa agggtctatt acatcacgag    120
ctcttcgggg tatggtgtgg gtaccatccc tgttcctctt aagaatagat gaaagggaag   180
gtcatctcat tccacccatg agacctacaa ttaagcactg tattggtatg tgaacgccag    240
tctggtaaat cgcgcccct tgttgcctca ggtttcacca caggtcataa atattgtacg    300
taagacaaat cctaagttag atgccgatat atccggcact cttcaagcat catagcaatg    360
gcgttttaaa tcacgcagtt aggttggtgt tcttctcatg tggtaaatcc tcaagggtgt    420
aactacaagt atacggtaga cttccaagat tggcaaaaaa agccagatcg agcgattttt    480
gcctggattt aaaggatcct ggagtgccaa ttaaacgtga gcaatatccc tctaacaaac    540
ttaccgagaa ttcctttgaa gggtacgtac agagtagtag ctccgctcta acagccgtga    600
gctcccatct ggcccattct ccacgcgaac caggctcatt cggacgataa gcaacaacac    660
ttctaattgg aagttgcaca tggcttcacg gcattgtctc catcattctt caaagaacca    720
attaatatga cgaaaaagaa atcctgcaag gttgagcgga caaatggctg gagcctcgag    780
agtgttgtgt gggtcaacgc gatttatttg cctcaacgct tggttaagcg gtgggacgcc    840
gtccagcctg aaggcttgcc ctaatttcga gcgtcccacc tcccagaatg agctgatttt    900
gggactccgc ggaaatcgct ggtgggttcc taggagcatt gcttattgtg acctttctcc    960
gaggcgttat atggtaacaa ggagttactg ccgtgaccta atagaatgtc cactgcccgc   1020
gcatgggtaa cacgtactgc gtgccatcat acgataggca agagtatttt agtgtggtgg   1080
attgcctcct tatttggagt taatgcactg gctgaccatt cgacttattc atactcagca   1140
tccttgttca tgctccctcc ctcgtaattt tactttcatt ggccttccct gccggtaaca   1200
```

```
tggcaaccat caccgaggtg cggacggatg cgctcgtccc aactgacctc gttcttaaga    1260
caggtcagat caaaatcgaa agcgaagaga tctcgacgag agacctgtct gatatccctc    1320
tgccaccgcc atcaaaacgg ccgacagaag tgctgagcgt agataaagga actccagata    1380
gccatgttcc tcgtgaccct cggcttatca gattaacggg tgttcatccg tttaatgttg    1440
agccacctct cacagatctg tataaagaag gtatgagtta aactgctcc  actcctatcc    1500 ttatcaggtt gcttgcaccg gctgtcatgc ttgtccccTT gagccgttac attctcacac    1560
tctgaaaggg ttttTaacat cgccggagct cttctatgtt cgaaatcatg gcccagtccc    1620
tcatatcaag gatgaagata tccctcactg ggaaattagc atcgaagggt tagtatagtg    1680
ctaggttctc tgccaaacat ccgttaacca agtatagac  tggtagagaa gcctttggta    1740
ctaaacttcc gacaagtgtt gcagcagtac gaccaaataa cagcgcctat cacccTcgta    1800
tgtgctggca atcgacgcaa agagcaaaac aatgtacgta aaacgaaagg tttttcctgg    1860
ggatcggcgg gactatcgac tgccctcttc actggcccat tgctggcgga tattctccgc    1920
agtgcgaaac ccctgcgtaa agcgaaatac gtctgtatgg aaggagcgga taagctggta    1980
tgctgtacct ctatcttatg atgataattg ctaagttcgc cgcagcccaa tggtcactac    2040
ggcacatcta tTaaattgaa ctgggccctg accccaaca  gggggatcat gcttgcacat    2100
aaaatgaacg gggagtctct tcgcccagat catggtcgtc cgctgagggc cgtcgtgccc    2160
ggtcaaatag gaggacgaag tgttaagtgg ctgaagaggc tgatcttgac cgatgcacca    2220
agcgacaact ggtaccatat caatgacaac cgcgtcttac cgtatgtcta aagggcactt    2280
attttatatt tccatcattt gtctaactcc ctaacccaga acaatggtct cgcctgagat    2340
ggcatcaaat aaccgaaatt ggtggcacga tgagcggtat gcgatttatg acctaaacac    2400
caactccgcc gttgcatatc cccaaaacaa tgaggtctta aatctcctgg tcgcagggcc    2460
gtcatatact gtcagaggat atgcatacgc cggtgggggc cgcagggtta ccagggtaga    2520 aatatccct  gacaaaggca aatgtacgca ccctcgctcg ctcgatgtgt gagaatgctt    2580
atcaaagcta acggacttat agcttggaga ttggcggaaa tcgaatatgc cgaagacaag    2640
tatcgtgatt ttgaaggcga gcttTTtgga ggcaaagtag atatgtactg cgcgaaact     2700 tgcttctgct ggtgtTTTtg gtctctaagc atcaccatcc cagagcttga gaacagtgat    2760
gccatccttg taagagccat ggacgaagca ttgggcgtgc agcctcgcga tatgtactgg    2820
tccgttctcg gaatgatgaa caacccgtgg ttccgggtta caattacgaa ggaaaacggg    2880
aacttgagat tcgagcaccc tacccacccT agtatgccta caggatggat ggaacgcgtc    2940
aaaaaggctg ggggtgacct gacgaatggt aactgggag  aaagacacga aggagaggag    3000
ccgacggagc cggagcccgt gcaagacatt aatatgaaga agacgggct  aagccgagtg    3060 attggtttTg aagaattcaa ggagaattcc tgcgatgaga agccatggtt catcgtgaat    3120
ggagaagtgt atgatggtca agcatttctt gaaggccacc ctggcggagc gcagagtatt    3180
atctcctctg ctggtctgga tgtctctgag gaattccttg ctattcgtga gtcccaaaaa    3240
tatcacactg caattgtacc atctattgac acctatccat agatagcgag acggcaaagg    3300
cgatgatgcc tgagtaccat attggaacga tggatccgga aggtttaaaa gcactcaagg    3360
atgatgcatc atcctccacc gatgaaattc gcccagtgtt cctccaatca cggtcttgga    3420
caaaggcaac attgaaagaa aggaaagaca tatcctggga tacacgaata tttagtttca    3480
aattggaaca cgaagatcaa acattgggtt taccagtcgg ccagcatctt atgatcaaag    3540
tcctcgacac atcatccaac aacgaagcca tcatccgctc atacacccca atttctgaaa    3600
```

```
ccagccagaa agggaccgtg gacttgctgg ttaaagtata ctttgcaaca gccacctcgg    3660
caggcggcaa gatgacgatg gccctggata ggctgccatt gggctccgtg gtggaatgca    3720
agggtccgac aggcagattc gaataccttg gaaatggacg agttgtcata agtgggaagg    3780
aacgccatgt tcggtcgttt aagatgattt gtggaggaac cggtatcaca ccgatcttcc    3840
aggtcttgcg cgccgtggtt caggaccggc aagatcccac ctcttgtaca gtcctcaatg    3900
gaaacagaca ggaggaagat atcctttgcc gggctgagct cgacggcttc atggcaaccg    3960
acagcagaag gtgtaatata atacacaccc tatccaaagc gccggactca tggactggcc    4020
gccgaggacg catatccgaa gagctcctaa aggagtacgc ggctccagaa gatgagagta    4080
tggtcctgat ttgtggtccg ccagccatgg aagaatcggc tcggaggata ctgttggcgg    4140
aaggatggaa agaatcagac cttcacttct tctaaattgg gattatccaa gggaatgact    4200
taatgagtat gtaagacatg ggtcataacg gcgttcgaaa catatacagg gttatgtttg    4260
ggaatagcac acgaataata acgttaatag gtaccaaagt ccttgataca ttagcacggt    4320
agaaaaagaa taatacaacg agctgggaat attctttaat ataaaactcc aagaagagct    4380
ggtgcggtgg agcttgtttt cgactctcag taatatttcc tcatatccaa gcgcgctagg    4440
aggtggtcga atacacatgt aggcgcttct ctggatgcaa aagtcgtgcc ggacctgccg    4500
aaagactttg aagatgcgtt cacgccatct aagttgcgta gataattcac aaaaagggat    4560
gtttgtttcc ggaatgtagc aaagagctga taggcaatag cctcagtttc gtggcgcacg    4620
ccgctcgttc catccatcct cgacaatgga gcaaatgtca aaatcgtacc gaaaatactt    4680
tccagcagct tcgctgcatc agcatgtctt ttgctgagaa agagcgcaaa aagcatttga    4740
tcgagaatat cttcatgata atctctaagt ctagggacag aatgtgctgc ttctatcgtg    4800
ccatcaatat caccgcggtc gaggcagcgt tcaatcttag ccaggctatc ttggaaccgc    4860
tgccaagtcg agccaatgcc gacatgaaag caataatcac tcaatgagag cacgaaatgc    4920
tggcagtcaa tgcgaaattt ctggtacacg tttcgagggt gcccagatag ggagtctctc    4980
cccgtagaat cacgaatgag acctttgacg accgaaacca ttcgaaggag tcgaagcaga    5040
tgcttgaaaa gacgatcata cttgttaagc gatcgcgacg taatgatagc ttccaggacg    5100
tctgatggtt tgtattgaag acgtaggaaa tccaaagctt                          5140
```

<210> SEQ ID NO 4
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
acgcgtcgac atgtactttc cagtgcgtgt agtctactct g                         41

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acgcctcgag ctgcagatcg gctgaagtta ggagcggcca ttgtc                     45

<210> SEQ ID NO 6
<211> LENGTH: 500
<212> TYPE: DNA
<213> ORGANISM: Aspergillus oryza

<400> SEQUENCE: 6

```
atgtactttc cagtgcgtgt agtctactct gacctcgtgt cacgattgtt gcttttgcct      60
gtctaaatgc gaccgtgctg tgcatgtttg ttaaatactg tcattcatct ttgtttcaac     120
aacaaagatt acatcaatta gtgctagcta gacaataact tttacagttg caacgttagt     180
cctagtatta tacatctcac cggatcctct tcaaacttca cggggtaacc aaaagaaagt     240
aacaagacta agcctattga tactgtggtt ctaatcttat tttagtttcc tgtacgtcca     300
ctgcaatcaa actaagtata catactacat cctagtatcc tacaccgtat ccttcaaccc     360
tagaacctcc cgctaggtat gtactgtaga tcgattatcc ggagattccc cgccacctgc     420
ttgaccaatc tgccgccctc agctgaaggc ccactggagt gaaaagacaa tggccgctcc     480
taacttcagc cgatctgcag                                                 500
```

<210> SEQ ID NO 7
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
aactgcagct gcagttatgt actccgtact cggttgaatt attaatc                    47
```

<210> SEQ ID NO 8
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
acgcgtcgac tttgggtggt ttggttggta ttctggttga gggttttgag                 50
```

<210> SEQ ID NO 9
<211> LENGTH: 1044
<212> TYPE: DNA
<213> ORGANISM: Aspergillus oryza

<400> SEQUENCE: 9

```
ctgcagttat gtactccgta ctcggttgaa ttattaatcg ggtattgcat taacttaatt      60
agctatgttc ttctttgttg aattagccct aactctgggt agagtgtggt ttttatagtg     120
acatgatggt ggaggaagga tttcttaatt actagggcag ggttattatg tggagtttag     180
ctcatttagg attcttgatg gaaggttctt atctccttgt caatatggta tcactcacat     240
atattcttga actatatctt cttgaattcc tcggctatcc tggtcagttc atgttcagta     300
ccgtagatag attgaattct ggtcgttcgt ttctactcct tcatcttcag tccattcagt     360
tccctaggtt gttggtctac cttccatggc cccggctgtt gtgggttgcg tcatgtagat     420
gaagggagct agccagatga taatatcaga gttctacaga gtaccatgct aagcctgggg     480
atttactggt taacatttgc ctagtaactt gtaagaatcg gaagtacttg gctccatgag     540
ccccacatta tgaaaaacaa tggcatcaac aaattgtctg tgcattatca tagtatagtt     600
```

```
ctgggtgggg gctatagtac ttgctggtac ttcatggagt gacaggctgt agtaggcggc      660
cttaataaaa cccagcagaa cgcattcatt agacagattt atctacgcat ataccagcta      720
acatagccta tttgtaatcc ttgtaatcca cactcaccta cgaatcacat agacgaaagg      780
aagaatgtgc tcagtggtgc gccaaaggtc ccccgaatcc cctcaaactc gctcatagtc      840
acatcccgcc aacatgattg gtaaaaatga aggtaccttg ggggtcctca gcatccattc      900
caggcttata ttctccctcg ccataatcat gaccagaact ccctcacaac ccctcttctc      960
cctcgtcctc gtcctcgcat ctcacctctc caactacaca tatactcaaa accctcaacc     1020
agaataccaa ccaaaccacc caaa                                            1044

<210> SEQ ID NO 10
<211> LENGTH: 1587
<212> TYPE: DNA
<213> ORGANISM: Aspergillus oryza

<400> SEQUENCE: 10
atgcggaaca accttctttt ttccctcaat gccattgctg gcgctgtcgc gcatccgtcc       60
ttccctatcc ataagaggca gtcggatctc aacgccttca ttgaggcaca gacacccatc      120
gccaaacagg gcgtcctcaa taatatcggc gctgatggca agcttgttga ggggggctgcc     180 gctggtatcg ttgtagcctc cccatccaag agtaatcccg actgttcgta caatcctacc      240
ctcaagaccg catgatatta ccacagagct aactatatat agacttctac acctggacgc      300
gcgacgctgg cctcaccatg gaagaagtga tagagcaatt catcggggga gatgcgactc      360
tcgagtccac aatccagaat tatgttgact ctcaagcgaa cgagcaggca gtctccaacc      420
catcaggcgg cctgtcggat ggctcgggtc ttgctgaacc caaattttac gtcaatatct      480
ctcaattcac cgattcttgg ggccgacccc agcgcgacgg gccagcctta cgtgcttccg      540
ctttgatcgc atatggcaac tctctgattt ccagcgacaa caatctgtt gtcaaagcta      600 acatctggcc aattgtccag aatgacttgt cttatgtggg tcaatactgg aaccagaccg      660
ggtttgatct ttgggaagag gttcagggca gctccttctt cactgttgct gtgcagcaca      720
aagccttggt ggagggcgat gcgtttgcaa aggcactcgg agaggaatgc caggcatgct      780
ccgtggcgcc tcaaatcctc tgccatcttc aggacttctg gaatgggtct gctgttcttt      840
ctaacttacc aaccaatggg cgcagtggac tggataccaa ctctcttttg ggctccattc      900
acacttttga tccagccgcc gcttgtgatg atacaacatt ccagccctgc tcctctcgcg      960
ccctgtcgaa ccataagctt gtggttgact ctttccggtc ggtctacggt atcaacaatg     1020
gacgtggagc aggaaaggcc gcggcagtgg gcccgtacgc agaggacacc tatcagggag     1080
gcaatccatg gttggtactc tgtctcatat ccaaagctta aactaatgaa tattaggtat     1140
cttaccaccc tggtcgctgc ggaattgctc tacgacgcct tgtatcagtg gacaaacaa     1200 ggtcaagtga acgtcactga aacttcccct cccttcttca aggacctctc cagcaatgtc     1260
accaccggat cctacgccaa gtcttcctca gcctatgagt cgcttacgag cgctgtcaag     1320
acctacgcag acggcttcat ctccgttgtc caggagtata ctcccgatgg cggtgctttg     1380
gctgagcagt acagtcggga ccagggcacc ccagtttcgg catccgatct gacttggtct     1440
tatgcagctt tcttgagtgc tgttggacga cgaaacggca ctgtccctgc tagctgggc      1500 tcttccacgg ccaacgcagt tccaagccaa tgttcggggg gtacagtttc tggaagttac     1560
actaccccaa ctgttgggtc gtggtag                                         1587
```

<210> SEQ ID NO 11
<211> LENGTH: 493
<212> TYPE: PRT
<213> ORGANISM: Aspergillus oryza

<400> SEQUENCE: 11

Met Arg Asn Asn Leu Leu Phe Ser Leu Asn Ala Ile Ala Gly Ala Val
1               5                   10                  15

Ala His Pro Ser Phe Pro Ile His Lys Arg Gln Ser Asp Leu Asn Ala
            20                  25                  30

Phe Ile Glu Ala Gln Thr Pro Ile Ala Lys Gln Gly Val Leu Asn Asn
        35                  40                  45

Ile Gly Ala Asp Gly Lys Leu Val Glu Gly Ala Ala Gly Ile Val
    50                  55                  60

Val Ala Ser Pro Ser Lys Ser Asn Pro Asp Tyr Phe Tyr Thr Trp Thr
65                  70                  75                  80

Arg Asp Ala Gly Leu Thr Met Glu Glu Val Ile Glu Gln Phe Ile Gly
                85                  90                  95

Gly Asp Ala Thr Leu Glu Ser Thr Ile Gln Asn Tyr Val Asp Ser Gln
            100                 105                 110

Ala Asn Glu Gln Ala Val Ser Asn Pro Ser Gly Gly Leu Ser Asp Gly
        115                 120                 125

Ser Gly Leu Ala Glu Pro Lys Phe Tyr Val Asn Ile Ser Gln Phe Thr
130                 135                 140

Asp Ser Trp Gly Arg Pro Gln Arg Asp Gly Pro Ala Leu Arg Ala Ser
145                 150                 155                 160

Ala Leu Ile Ala Tyr Gly Asn Ser Leu Ile Ser Ser Asp Lys Gln Ser
                165                 170                 175

Val Val Lys Ala Asn Ile Trp Pro Ile Val Gln Asn Asp Leu Ser Tyr
            180                 185                 190

Val Gly Gln Tyr Trp Asn Gln Thr Gly Phe Asp Leu Trp Glu Glu Val
        195                 200                 205

Gln Gly Ser Ser Phe Phe Thr Val Ala Val Gln His Lys Ala Leu Val
210                 215                 220

Glu Gly Asp Ala Phe Ala Lys Ala Leu Gly Glu Glu Cys Gln Ala Cys
225                 230                 235                 240

Ser Val Ala Pro Gln Ile Leu Cys His Leu Gln Asp Phe Trp Asn Gly
                245                 250                 255

Ser Ala Val Leu Ser Asn Leu Pro Thr Asn Gly Arg Ser Gly Leu Asp
            260                 265                 270

Thr Asn Ser Leu Leu Gly Ser Ile His Thr Phe Asp Pro Ala Ala Ala
        275                 280                 285

Cys Asp Asp Thr Thr Phe Gln Pro Cys Ser Ser Arg Ala Leu Ser Asn
290                 295                 300

His Lys Leu Val Val Asp Ser Phe Arg Ser Val Tyr Gly Ile Asn Asn
305                 310                 315                 320

Gly Arg Gly Ala Gly Lys Ala Ala Val Gly Pro Tyr Ala Glu Asp
                325                 330                 335

Thr Tyr Gln Gly Gly Asn Pro Trp Tyr Leu Thr Thr Val Ala Ala
            340                 345                 350

Glu Leu Leu Tyr Asp Ala Leu Tyr Gln Trp Asp Lys Gln Gly Gln Val
        355                 360                 365

Asn Val Thr Glu Thr Ser Leu Pro Phe Phe Lys Asp Leu Ser Ser Asn
370                 375                 380

```
Val Thr Thr Gly Ser Tyr Ala Lys Ser Ser Ala Tyr Glu Ser Leu
385                 390                 395                 400

Thr Ser Ala Val Lys Thr Tyr Ala Asp Gly Phe Ile Ser Val Val Gln
            405                 410                 415

Glu Tyr Thr Pro Asp Gly Gly Ala Leu Ala Glu Gln Tyr Ser Arg Asp
        420                 425                 430

Gln Gly Thr Pro Val Ser Ala Ser Asp Leu Thr Trp Ser Tyr Ala Ala
        435                 440                 445

Phe Leu Ser Ala Val Gly Arg Arg Asn Gly Thr Val Pro Ala Ser Trp
    450                 455                 460

Gly Ser Ser Thr Ala Asn Ala Val Pro Ser Gln Cys Ser Gly Gly Thr
465                 470                 475                 480

Val Ser Gly Ser Tyr Thr Thr Pro Thr Val Gly Ser Trp
                485                 490

<210> SEQ ID NO 12
<211> LENGTH: 1608
<212> TYPE: DNA
<213> ORGANISM: Aspergillus oryza

<400> SEQUENCE: 12
atgcggaaca accttctttt ttccctcaat gccattgctg gcgctgtcgc gcatccgtcc      60
ttccctatcc ataagaggca gtcggatctc aacgccttca ttgaggcaca gacacccatc     120
gccaaacagg gcgtcctcaa taatatcggc gctgatggca agcttgttga ggggggctgcc    180
gctggtatcg ttgtagcctc cccatccaag agtaatcccg actgttcgta caatcctacc     240
ctcaagaccg catgatatta ccacagagct aactatatat agacttctac acctggacgc     300
gcgacgctgg cctcaccatg gaagaagtga tagagcaatt catcggggga gatgcgactc     360
tcgagtccac aatccagaat tatgttgact ctcaagcgaa cgagcaggca gtctccaacc     420
catcaggcgg cctgtcggat ggctcgggtc ttgctgaacc caaattttac gtcaatatct     480
ctcaattcac cgattcttgg ggccgacccc agcgcgacgg ccagccttac gtgcttccg      540
ctttgatcgc atatggcaac tctctgattt ccagcgacaa caatctgtt gtcaaagcta      600
acatctggcc aattgtccag aatgacttgt cttatgtggg tcaatactgg aaccagaccg     660
ggtttgatct tgggaagag gttcagggca gctccttctt cactgttgct gtgcagcaca      720
aagccttggt ggagggcgat gcgtttgcaa aggcactcgg agaggaatgc caggcatgct     780
ccgtggcgcc tcaaatcctc tgccatcttc aggacttctg gaatgggtct gctgttcttt     840
ctaacttacc aaccaatggg cgcagtggac tggataccaa ctctctttg ggctccattc      900
acactttga tccagccgcc gcttgtgatg atacaacatt ccagccctgc tcctctcgcg      960
ccctgtcgaa ccataagctt gtggttgact ctttccggtc ggtctacggt atcaacaatg    1020
gacgtggagc aggaaaggcc gcggcagtgg cccgtacgc agaggacacc tatcagggag     1080
gcaatccatg gttggtactc tgtctcatat ccaaagctta actaatgaa tattaggtat     1140
cttaccaccc tggtcgctgc ggaattgctc tacgacgcct tgtatcagtg gacaaacaa     1200
ggtcaagtga acgtcactga aacttcccct cccttcttca aggacctctc cagcaatgtc    1260
accaccggat cctacgccaa gtcttcctca gcctatgagt cgcttacgag cgctgtcaag    1320
acctacgcag acggcttcat ctccgttgtc caggagtata ctcccgatgg cggtgctttg    1380
gctgagcagt acagtcggga ccagggcacc ccagttcgg catccgatct gacttggtct    1440
tatgcagctt tcttgagtgc tgttggacga cgaaacggca ctgtcctgc tagctgggc     1500
```

```
tcttccacgg ccaacgcagt tccaagccaa tgttcggggg gtacagtttc tggaagttac    1560
actaccccaa ctgttgggtc gtggcatcac catcaccatc accactag                 1608
```

<210> SEQ ID NO 13
<211> LENGTH: 500
<212> TYPE: PRT
<213> ORGANISM: Aspergillus oryza

<400> SEQUENCE: 13

```
Met Arg Asn Asn Leu Leu Phe Ser Leu Asn Ala Ile Ala Gly Ala Val
1               5                   10                  15

Ala His Pro Ser Phe Pro Ile His Lys Arg Gln Ser Asp Leu Asn Ala
            20                  25                  30

Phe Ile Glu Ala Gln Thr Pro Ile Ala Lys Gln Gly Val Leu Asn Asn
        35                  40                  45

Ile Gly Ala Asp Gly Lys Leu Val Glu Gly Ala Ala Gly Ile Val
    50                  55                  60

Val Ala Ser Pro Ser Lys Ser Asn Pro Asp Tyr Phe Tyr Thr Trp Thr
65                  70                  75                  80

Arg Asp Ala Gly Leu Thr Met Glu Glu Val Ile Glu Gln Phe Ile Gly
                85                  90                  95

Gly Asp Ala Thr Leu Glu Ser Thr Ile Gln Asn Tyr Val Asp Ser Gln
            100                 105                 110

Ala Asn Glu Gln Ala Val Ser Asn Pro Ser Gly Gly Leu Ser Asp Gly
        115                 120                 125

Ser Gly Leu Ala Glu Pro Lys Phe Tyr Val Asn Ile Ser Gln Phe Thr
    130                 135                 140

Asp Ser Trp Gly Arg Pro Gln Arg Asp Gly Pro Ala Leu Arg Ala Ser
145                 150                 155                 160

Ala Leu Ile Ala Tyr Gly Asn Ser Leu Ile Ser Ser Asp Lys Gln Ser
                165                 170                 175

Val Val Lys Ala Asn Ile Trp Pro Ile Val Gln Asn Asp Leu Ser Tyr
            180                 185                 190

Val Gly Gln Tyr Trp Asn Gln Thr Gly Phe Asp Leu Trp Glu Val
        195                 200                 205

Gln Gly Ser Ser Phe Phe Thr Val Ala Val Gln His Lys Ala Leu Val
    210                 215                 220

Glu Gly Asp Ala Phe Ala Lys Ala Leu Gly Glu Glu Cys Gln Ala Cys
225                 230                 235                 240

Ser Val Ala Pro Gln Ile Leu Cys His Leu Gln Asp Phe Trp Asn Gly
                245                 250                 255

Ser Ala Val Leu Ser Asn Leu Pro Thr Asn Gly Arg Ser Gly Leu Asp
            260                 265                 270

Thr Asn Ser Leu Leu Gly Ser Ile His Thr Phe Asp Pro Ala Ala Ala
        275                 280                 285

Cys Asp Asp Thr Thr Phe Gln Pro Cys Ser Ser Arg Ala Leu Ser Asn
    290                 295                 300

His Lys Leu Val Val Asp Ser Phe Arg Ser Val Tyr Gly Ile Asn Asn
305                 310                 315                 320

Gly Arg Gly Ala Gly Lys Ala Ala Val Gly Pro Tyr Ala Glu Asp
                325                 330                 335

Thr Tyr Gln Gly Gly Asn Pro Trp Tyr Leu Thr Thr Leu Val Ala Ala
            340                 345                 350
```

```
Glu Leu Leu Tyr Asp Ala Leu Tyr Gln Trp Asp Lys Gln Gly Gln Val
            355                 360                 365

Asn Val Thr Glu Thr Ser Leu Pro Phe Phe Lys Asp Leu Ser Ser Asn
        370                 375                 380

Val Thr Thr Gly Ser Tyr Ala Lys Ser Ser Ala Tyr Glu Ser Leu
385                 390                 395                 400

Thr Ser Ala Val Lys Thr Tyr Ala Asp Gly Phe Ile Ser Val Val Gln
                405                 410                 415

Glu Tyr Thr Pro Asp Gly Gly Ala Leu Ala Glu Gln Tyr Ser Arg Asp
            420                 425                 430

Gln Gly Thr Pro Val Ser Ala Ser Asp Leu Thr Trp Ser Tyr Ala Ala
        435                 440                 445

Phe Leu Ser Ala Val Gly Arg Arg Asn Gly Thr Val Pro Ala Ser Trp
    450                 455                 460

Gly Ser Ser Thr Ala Asn Ala Val Pro Ser Gln Cys Ser Gly Gly Thr
465                 470                 475                 480

Val Ser Gly Ser Tyr Thr Thr Pro Thr Val Gly Ser Trp His His His
                485                 490                 495

His His His His
        500

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atgcggaaca accttctttt ttccctcaat                                    30

<210> SEQ ID NO 15
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctagtggtga tggtgatggt gatgccacga cccaacagtt ggggtagtg               49

<210> SEQ ID NO 16
<211> LENGTH: 1161
<212> TYPE: DNA
<213> ORGANISM: Xenopus laevis

<400> SEQUENCE: 16
ctcgagcagg gggatcatct aatcaagcac aaataagggg cgtgtaacac aaaagccagc   60
gaccctttcc aatgcaaatc aaacttgcaa ttctttgccg ttttatcat ttaagtgtcg   120 gcttaaggtc cactatcaga tgtaaacagc cttatctaac aaaggtatca ttacattctg  180
aaattctcag gcatgcaagc tagcttatga cgcactaggg agtgccaccc ttcctttcgc  240
cctaacttcg tgataactcg cgcgtttcac tcaacagctg catccgccct agtgctactg  300
ggagttgtag tatacaagac gcttacaggc tgaatgttct gtcaagaccc gcctctagc   360 actttgggaa ttctggactt gatgatgtca tggttaatcc ccgcccagta gaggcggcta  420
tataaagggt ggttaaggcc cggttcgctc tcttcctcac cgggtctgcg gcgagttcta  480
```

```
gctgaagctt cctgcaggtc gaccgatcct gagaacttca gggtgagttt ggggacccct     540
gattgttctt tctttttcgc tattgtaaaa ttcatgttat atggagggg caaagttttc      600 agggtgttgt ttagaatggg aagatgtccc ttgtatcacc atggaccctc atgataattt     660
tgtttctttc actttctact ctgttgacaa ccattgtctc ctcttatttt cttttcattt     720
tctgtaactt tttcgttaaa ctttagcttg catttgtaac gaattttta attcacttt      780 gtttatttgt cagattgtaa gtactttctc taatcacttt ttttcaagg caatcagggt      840 atattatatt gtacttcagc acagttttag agaacaattg ttataattaa atgataaggt     900
agaatatttc tgcatataaa ttctggctgg cgtggaaata ttcttattgg tagaaacaac     960
tacaccctgg tcatcatcct gcctttctct ttatggttac aatgatatac actgtttgag    1020
atgaggataa aatactctga gtccaaaccg ggcccctctg ctaaccatgt tcatgccttc    1080
ttctctttcc tacagctcct gggcaacgtg ctggttgttg tgctgtctca tcattttggc    1140
aaagaattcc tcgacggatc c                                              1161
```

<210> SEQ ID NO 17
<211> LENGTH: 720
<212> TYPE: DNA
<213> ORGANISM: Aequorea victoria

<400> SEQUENCE: 17

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720
```

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 18

```
aaaaaacccg gggtgagcaa gggcgaggag                                       30
```

<210> SEQ ID NO 19
<211> LENGTH: 41
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 19
ctagtggtgg tgatgatgat gcttgtacag ctcgtccatg c                41

<210> SEQ ID NO 20
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ttttggccga ggcggcctag tggtggtgat gatgatg                     37

<210> SEQ ID NO 21
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aaaaaaggcc gcctcggccg taatctctgc ttaaaagcac agaatc           46

<210> SEQ ID NO 22
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22 tttttttcccg ggcactttgt gattcatggt gtattacc                   38

<210> SEQ ID NO 23
<211> LENGTH: 485
<212> TYPE: DNA
<213> ORGANISM: Homo sapiens

<400> SEQUENCE: 23
atccatcaca ctccttctac aatttgagta aagtgactca catagaaatt cggaatacca    60
ggaacttaac ttacatagac cctgatgccc tcaaagagct cccccctccta aagttccttg   120 gcattttcaa cactggactt aaaatgttcc ctgacctgac caaagtttat tccactgata   180
tattctttat acttgaaatt acagacaacc cttacatgac gtcaatccct gtgaatgctt   240
ttcagggact atgcaatgaa accttgacac tgaagctgta caacaacggc tttacttcag   300
tccaaggata tgctttcaat gggacaaagc tggatgctgt ttacctaaac aagaataaat   360
acctgacagt tattgacaaa gatgcatttg gaggagtata cagtggacca agcttgctgg   420
acgtgtctca aaccagtgtc actgcccttc catccaaagg cctggagcac ctgaaggaac   480
tgata                                                               485

<210> SEQ ID NO 24
<211> LENGTH: 1980
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS -continued

<220> LOCATION: (16)..(1953)

<400> SEQUENCE: 24

```
aagaggtaat acacc atg aat cac aaa gtg cat cat cat cat cat cac atg        51
                 Met Asn His Lys Val His His His His His His Met
                  1               5                  10 caa gtt tca gtt gaa acc act caa ggc ctt ggc cgc cgt gta acg att         99
Gln Val Ser Val Glu Thr Thr Gln Gly Leu Gly Arg Arg Val Thr Ile
         15                  20                  25 act atc gct gct gac agc atc gag acc gct gtt aaa agc gag ctg gtc        147
Thr Ile Ala Ala Asp Ser Ile Glu Thr Ala Val Lys Ser Glu Leu Val
     30                  35                  40 aac gtt gcg aaa aaa gta cgt att gac ggc ttc cgc aag ggc aaa gtg        195
Asn Val Ala Lys Lys Val Arg Ile Asp Gly Phe Arg Lys Gly Lys Val
 45                  50                  55                  60 cca atg aat atc gtt gct cag cgt tat ggc gcg tct gta cgc cag gac        243
Pro Met Asn Ile Val Ala Gln Arg Tyr Gly Ala Ser Val Arg Gln Asp
                 65                  70                  75 gtt ctg ggt gac ctg atg agc cgt aac ttc att gac gcc atc att aaa        291
Val Leu Gly Asp Leu Met Ser Arg Asn Phe Ile Asp Ala Ile Ile Lys
             80                  85                  90 gaa aaa atc aat ccg gct ggc gca ccg act tat gtt ccg ggc gaa tac        339
Glu Lys Ile Asn Pro Ala Gly Ala Pro Thr Tyr Val Pro Gly Glu Tyr
         95                 100                 105 aag ctg ggt gaa gac ttc act tac tct gta gag ttt gaa gtt tat ccg        387
Lys Leu Gly Glu Asp Phe Thr Tyr Ser Val Glu Phe Glu Val Tyr Pro
    110                 115                 120 gaa gtt gaa ctg caa ggt ctg gaa gcg atc gaa gtt gaa aaa ccg atc        435
Glu Val Glu Leu Gln Gly Leu Glu Ala Ile Glu Val Glu Lys Pro Ile
125                 130                 135                 140 gtt gaa gtg acc gac gct gac gtt gac ggc atg ctg gat act ctg cgt        483
Val Glu Val Thr Asp Ala Asp Val Asp Gly Met Leu Asp Thr Leu Arg
                145                 150                 155 aaa cag cag gcg acc tgg aaa gaa aaa gac ggc gct gtt gaa gca gaa        531
Lys Gln Gln Ala Thr Trp Lys Glu Lys Asp Gly Ala Val Glu Ala Glu
            160                 165                 170 gac cgc gtg acc atc gac ttc acc ggt tct gta gac ggc gaa gag ttc        579
Asp Arg Val Thr Ile Asp Phe Thr Gly Ser Val Asp Gly Glu Glu Phe
        175                 180                 185 gaa ggc ggt aaa gcg tct gat ttc gta ctg gcg atg ggc cag ggt cgt        627
Glu Gly Gly Lys Ala Ser Asp Phe Val Leu Ala Met Gly Gln Gly Arg
    190                 195                 200 atg atc ccg ggc ttt gaa gac ggt atc aaa ggc cac aaa gct ggc gaa        675
Met Ile Pro Gly Phe Glu Asp Gly Ile Lys Gly His Lys Ala Gly Glu
205                 210                 215                 220 gag ttc acc atc gac gtg acc ttc ccg gaa gaa tac cac gca gaa aac        723
Glu Phe Thr Ile Asp Val Thr Phe Pro Glu Glu Tyr His Ala Glu Asn
                225                 230                 235 ctg aaa ggt aaa gca gcg aaa ttc gct atc aac ctg aag aaa gtt gaa        771
Leu Lys Gly Lys Ala Ala Lys Phe Ala Ile Asn Leu Lys Lys Val Glu
            240                 245                 250 gag cgt gaa ctg ccg gaa ctg acc gca gag ttc atc aaa cgt ttc ggc        819
Glu Arg Glu Leu Pro Glu Leu Thr Ala Glu Phe Ile Lys Arg Phe Gly
        255                 260                 265 gtt gaa gat ggt tcc gta gaa ggt ctg cgc gct gaa gtg cgt aaa aac        867
Val Glu Asp Gly Ser Val Glu Gly Leu Arg Ala Glu Val Arg Lys Asn
    270                 275                 280 atg gag cgc gag ctg aag agc gcc atc cgt aac cgc gtt aag tct cag        915
Met Glu Arg Glu Leu Lys Ser Ala Ile Arg Asn Arg Val Lys Ser Gln
285                 290                 295                 300
```

```
gcg atc gaa ggt ctg gta aaa gct aac gac atc gac gta ccg gct gcg      963
Ala Ile Glu Gly Leu Val Lys Ala Asn Asp Ile Asp Val Pro Ala Ala
            305                 310                 315 ctg atc gac agc gaa atc gac gtt ctg cgt cgc cag gct gca cag cgt     1011
Leu Ile Asp Ser Glu Ile Asp Val Leu Arg Arg Gln Ala Ala Gln Arg
            320                 325                 330 ttc ggt ggc aac gaa aaa caa gct ctg gaa ctg ccg cgc gaa ctg ttc     1059
Phe Gly Gly Asn Glu Lys Gln Ala Leu Glu Leu Pro Arg Glu Leu Phe
            335                 340                 345 gaa gaa cag gct aaa cgc cgc gta gtt gtt ggc ctg ctg ctg ggc gaa     1107
Glu Glu Gln Ala Lys Arg Arg Val Val Val Gly Leu Leu Leu Gly Glu
        350                 355                 360 gtt atc cgc acc aac gag ctg aaa gct gac gaa gag cgc gtg aaa ggc     1155
Val Ile Arg Thr Asn Glu Leu Lys Ala Asp Glu Glu Arg Val Lys Gly
365                 370                 375                 380 ctg atc gaa gag atg gct tct gcg tac gaa gat ccg aaa gaa gtt atc     1203
Leu Ile Glu Glu Met Ala Ser Ala Tyr Glu Asp Pro Lys Glu Val Ile
                385                 390                 395 gag ttc tac agc aaa aac aaa gaa ctg atg gac aac atg cgc aat gtt     1251
Glu Phe Tyr Ser Lys Asn Lys Glu Leu Met Asp Asn Met Arg Asn Val
                400                 405                 410 gct ctg gaa gaa cag gct gtt gaa gct gta ctg gcg aaa gcg aaa gtg     1299
Ala Leu Glu Glu Gln Ala Val Glu Ala Val Leu Ala Lys Ala Lys Val
            415                 420                 425 act gaa aaa gaa acc act ttc aac gag ctg atg aac cag cag gcg tcc     1347
Thr Glu Lys Glu Thr Thr Phe Asn Glu Leu Met Asn Gln Gln Ala Ser
        430                 435                 440 gcg ggt ctg gaa gtt ctg ttc cag ggg ccc tcc gcg ggt ctg gtg cca     1395
Ala Gly Leu Glu Val Leu Phe Gln Gly Pro Ser Ala Gly Leu Val Pro
445                 450                 455                 460 cgc ggt agt ggt ggt atc gaa ggt agg cat ata tgg agc tcg gta ccc     1443
Arg Gly Ser Gly Gly Ile Glu Gly Arg His Ile Trp Ser Ser Val Pro
                465                 470                 475 tcg agg gat cca tca cac tcc ttc tac aat ttg agt aaa gtg act cac     1491
Ser Arg Asp Pro Ser His Ser Phe Tyr Asn Leu Ser Lys Val Thr His
                480                 485                 490 ata gaa att cgg aat acc agg aac tta act tac ata gac cct gat gcc     1539
Ile Glu Ile Arg Asn Thr Arg Asn Leu Thr Tyr Ile Asp Pro Asp Ala
            495                 500                 505 ctc aaa gag ctc ccc ctc cta aag ttc ctt ggc att ttc aac act gga     1587
Leu Lys Glu Leu Pro Leu Leu Lys Phe Leu Gly Ile Phe Asn Thr Gly
        510                 515                 520 ctt aaa atg ttc cct gac ctg acc aaa gtt tat tcc act gat ata ttc     1635
Leu Lys Met Phe Pro Asp Leu Thr Lys Val Tyr Ser Thr Asp Ile Phe
525                 530                 535                 540 ttt ata ctt gaa att aca gac aac cct tac atg acg tca atc cct gtg     1683
Phe Ile Leu Glu Ile Thr Asp Asn Pro Tyr Met Thr Ser Ile Pro Val
                545                 550                 555 aat gct ttt cag gga cta tgc aat gaa acc ttg aca ctg aag ctg tac     1731
Asn Ala Phe Gln Gly Leu Cys Asn Glu Thr Leu Thr Leu Lys Leu Tyr
            560                 565                 570 aac aac ggc ttt act tca gtc caa gga tat gct ttc aat ggg aca aag     1779
Asn Asn Gly Phe Thr Ser Val Gln Gly Tyr Ala Phe Asn Gly Thr Lys
        575                 580                 585 ctg gat gct gtt tac cta aac aag aat aaa tac ctg aca gtt att gac     1827
Leu Asp Ala Val Tyr Leu Asn Lys Asn Lys Tyr Leu Thr Val Ile Asp
        590                 595                 600 aaa gat gca ttt gga gga gta tac agt gga cca agc ttg ctg gac gtg     1875
Lys Asp Ala Phe Gly Gly Val Tyr Ser Gly Pro Ser Leu Leu Asp Val
```

```
                605               610               615               620
tct caa acc agt gtc act gcc ctt cca tcc aaa ggc ctg gag cac ctg    1923
Ser Gln Thr Ser Val Thr Ala Leu Pro Ser Lys Gly Leu Glu His Leu
                625               630               635 aag gaa ctg ata ctc gac ctg cag tct aga taggtaatct ctgcttaaaa      1973
Lys Glu Leu Ile Leu Asp Leu Gln Ser Arg
                640               645 gcacaga                                                            1980
```

<210> SEQ ID NO 25
<211> LENGTH: 646
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Met Asn His Lys Val His His His His His Met Gln Val Ser Val
1               5                   10                  15

Glu Thr Thr Gln Gly Leu Gly Arg Arg Val Thr Ile Thr Ile Ala Ala
                20                  25                  30

Asp Ser Ile Glu Thr Ala Val Lys Ser Glu Leu Val Asn Val Ala Lys
            35                  40                  45

Lys Val Arg Ile Asp Gly Phe Arg Lys Gly Lys Val Pro Met Asn Ile
50                  55                  60

Val Ala Gln Arg Tyr Gly Ala Ser Val Arg Gln Asp Val Leu Gly Asp
65                  70                  75                  80

Leu Met Ser Arg Asn Phe Ile Asp Ala Ile Ile Lys Glu Lys Ile Asn
                85                  90                  95

Pro Ala Gly Ala Pro Thr Tyr Val Pro Gly Glu Tyr Lys Leu Gly Glu
            100                 105                 110

Asp Phe Thr Tyr Ser Val Glu Phe Glu Val Tyr Pro Glu Val Glu Leu
        115                 120                 125

Gln Gly Leu Glu Ala Ile Glu Val Glu Lys Pro Ile Val Glu Val Thr
    130                 135                 140

Asp Ala Asp Val Asp Gly Met Leu Asp Thr Leu Arg Lys Gln Gln Ala
145                 150                 155                 160

Thr Trp Lys Glu Lys Asp Gly Ala Val Glu Ala Glu Asp Arg Val Thr
                165                 170                 175

Ile Asp Phe Thr Gly Ser Val Asp Gly Glu Glu Phe Glu Gly Gly Lys
            180                 185                 190

Ala Ser Asp Phe Val Leu Ala Met Gly Gln Gly Arg Met Ile Pro Gly
        195                 200                 205

Phe Glu Asp Gly Ile Lys Gly His Lys Ala Gly Glu Glu Phe Thr Ile
    210                 215                 220

Asp Val Thr Phe Pro Glu Glu Tyr His Ala Glu Asn Leu Lys Gly Lys
225                 230                 235                 240

Ala Ala Lys Phe Ala Ile Asn Leu Lys Lys Val Glu Glu Arg Glu Leu
                245                 250                 255

Pro Glu Leu Thr Ala Glu Phe Ile Lys Arg Phe Gly Val Glu Asp Gly
            260                 265                 270

Ser Val Glu Gly Leu Arg Ala Glu Val Arg Lys Asn Met Glu Arg Glu
        275                 280                 285

Leu Lys Ser Ala Ile Arg Asn Arg Val Lys Ser Gln Ala Ile Glu Gly
    290                 295                 300
```

```
Leu Val Lys Ala Asn Asp Ile Asp Val Pro Ala Ala Leu Ile Asp Ser
305                 310                 315                 320

Glu Ile Asp Val Leu Arg Arg Gln Ala Ala Gln Arg Phe Gly Gly Asn
            325                 330                 335

Glu Lys Gln Ala Leu Glu Leu Pro Arg Glu Leu Phe Glu Glu Gln Ala
        340                 345                 350

Lys Arg Arg Val Val Val Gly Leu Leu Leu Gly Glu Val Ile Arg Thr
            355                 360                 365

Asn Glu Leu Lys Ala Asp Glu Glu Arg Val Lys Gly Leu Ile Glu Glu
370                 375                 380

Met Ala Ser Ala Tyr Glu Asp Pro Lys Glu Val Ile Glu Phe Tyr Ser
385                 390                 395                 400

Lys Asn Lys Glu Leu Met Asp Asn Met Arg Asn Val Ala Leu Glu Glu
            405                 410                 415

Gln Ala Val Glu Ala Val Leu Ala Lys Ala Lys Val Thr Glu Lys Glu
        420                 425                 430

Thr Thr Phe Asn Glu Leu Met Asn Gln Gln Ala Ser Ala Gly Leu Glu
            435                 440                 445

Val Leu Phe Gln Gly Pro Ser Ala Gly Leu Val Pro Arg Gly Ser Gly
450                 455                 460

Gly Ile Glu Gly Arg His Ile Trp Ser Ser Val Pro Ser Arg Asp Pro
465                 470                 475                 480

Ser His Ser Phe Tyr Asn Leu Ser Lys Val Thr His Ile Glu Ile Arg
            485                 490                 495

Asn Thr Arg Asn Leu Thr Tyr Ile Asp Pro Asp Ala Leu Lys Glu Leu
        500                 505                 510

Pro Leu Leu Lys Phe Leu Gly Ile Phe Asn Thr Gly Leu Lys Met Phe
            515                 520                 525

Pro Asp Leu Thr Lys Val Tyr Ser Thr Asp Ile Phe Phe Ile Leu Glu
        530                 535                 540

Ile Thr Asp Asn Pro Tyr Met Thr Ser Ile Pro Val Asn Ala Phe Gln
545                 550                 555                 560

Gly Leu Cys Asn Glu Thr Leu Thr Leu Lys Leu Tyr Asn Asn Gly Phe
            565                 570                 575

Thr Ser Val Gln Gly Tyr Ala Phe Asn Gly Thr Lys Leu Asp Ala Val
        580                 585                 590

Tyr Leu Asn Lys Asn Lys Tyr Leu Thr Val Ile Asp Lys Asp Ala Phe
            595                 600                 605

Gly Gly Val Tyr Ser Gly Pro Ser Leu Leu Asp Val Ser Gln Thr Ser
        610                 615                 620

Val Thr Ala Leu Pro Ser Lys Gly Leu Glu His Leu Lys Glu Leu Ile
625                 630                 635                 640

Leu Asp Leu Gln Ser Arg
            645

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

-continued

```
<400> SEQUENCE: 26

His His His His His His
1               5
```